(12) United States Patent
Klein et al.

(10) Patent No.: US 9,050,315 B2
(45) Date of Patent: Jun. 9, 2015

(54) IN VIVO AND EX VIVO EXPANSION OF HEMATOPOIETIC STEM CELLS WITH A TARGETED COMBINATION OF CLINICALLY TESTED, FDA APPROVED DRUGS

(75) Inventors: Peter S. Klein, Wynnewood, PA (US); Jian Huang, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 293 days.

(21) Appl. No.: 13/084,180

(22) Filed: Apr. 11, 2011

(65) Prior Publication Data
US 2011/0251593 A1 Oct. 13, 2011

Related U.S. Application Data

(60) Provisional application No. 61/323,203, filed on Apr. 12, 2010.

(51) Int. Cl.
*A61K 35/28* (2006.01)
*C12N 5/0789* (2010.01)

(52) U.S. Cl.
CPC .............. *A61K 35/28* (2013.01); *C12N 5/0647* (2013.01); *C12N 2501/04* (2013.01); *C12N 2501/415* (2013.01)

(58) Field of Classification Search
CPC .. A61K 35/28; C12N 5/0647; C12N 2501/04; C12N 2501/415
See application file for complete search history.

(56) References Cited

U.S. PATENT DOCUMENTS

2010/0099186 A1* 4/2010 Perry et al. .................... 435/373

OTHER PUBLICATIONS

Huang et al. Pivotal role for glycogen synthase kinase-3 in hematopoietic stem cell homeostasis in mice. J. Clin. Invest. 119:3519-3529 (2009).*
Rapamycin. Sigma-Aldrich Product information. dated Oct. 20, 1998. downloaded on Jun. 26, 2014 from http://www.sigmaaldrich.com/content/dam/sigma-aldrich/docs/Sigma/Product_Information_Sheet/1/r0395pis.pdf. p. 1-2.*
Austin, et al., "A role for the Wnt gene family in hematopoiesis: expansion of multilineage progenitor cells." 1997, Blood. 89:3624-3635.
Baba, et al., "Constitutively active beta-catenin promotes expansion of multipotent hematopoietic progenitors in culture." 2006, J. Immunol. 177:2294-2303.
Ballin, et al., "Increased number of peripheral blood CD34+ cells in lithium-treated patients." 1998. Br. J. Haematol. 100:219-221.
Boggs, et al., "The hematopoietic effects of lithium." 1983. Semin. Hematol. 20:129-138.
Chen, et al., "TSC-mTOR maintains quiescence and function of hematopoietic stem cells by repressing mitochondrial biogenesis and reactive oxygen species." 2008, J. Exp. Med. 205:2397-2408.
Cobas, et al., "Beta-catenin is dispensable for hematopoiesis and lymphopoiesis." 2004, J. Exp. Med. 199:221-229.
Doble, et al., "Functional redundancy of GSK-3alpha and GSK-3beta in Wnt/beta-catenin signaling shown by using an allelic series of embryonic stem cell lines." 2007, Dev. Cell. 12:957-971.
Fleming, et al., "Wnt signaling in the niche enforces hematopoietic stem cell quiescence and is necessary to preserve self-renewal in vivo." 2008, Cell Stem Cell. 2:274-283.
Focosi, et al,, "Lithium and hematology: established and proposed uses." 2009, J. Leukoc. Biol. 85:20-28.
Gan, et al., "mTORC1-dependent and -independent regulation of stem cell renewal, differentiation, and mobilization." 2008, Proc. Natl. Acad. Sci. U. S. A. 105:19384-19389.
Goessling, et al., "Genetic interaction of PGE2 and Wnt signaling regulates developmental specification of stem cells and regeneration." 2009, Cell. 136:1136-1147.
Hedgepeth, et al., "Activation of the Wnt signaling pathway: a molecular mechanism for lithium action." 1997, Dev. Biol. 185:82-91.
Holmes, et al., "Glycogen synthase kinase-3beta inhibition preserves hematopoietic stem cell activity and inhibits leukemic cell growth." 2008, Stem Cells. 26:1288-1297.
Inoki, et al., "TSC2 integrates Wnt and energy signals via a coordinated phosphorylation by AMPK and GSK3 to regulate cell growth." 2006, Cell. 126:955-968.
Jeannet, et al., "Long-term, multilineage hematopoiesis occurs in the combined absence of beta-catenin and gamma-catenin." 2008, Blood. 111:142-149.
Joyce, "Sequential effects of lithium on haematopoiesis." 1984, Br. J. Haematol. 56:307-321.
Kirstetter et al., "Activation of the canonical Wnt pathway leads to loss of hematopoietic stem cell repopulation and multilineage differentiation block." 2006, Nat. Immunol. 7:1048-1056.
Klein, et al., "A molecular mechanism for the effect of lithium on development." 1996, Proc. Natl. Acad. Sci. U. S. A. 93:8455-8459.
Koch, et al., "Simultaneous loss of beta- and gamma-catenin does not perturb hematopoiesis or lymphopoiesis." 2008, Blood. 111:160-164.
Levitt, et al., "The effect of lithium on murine hematopoiesis in a liquid culture system." 1980, New England Journal of Medicine 302:713-719.
Luis, et al., "Wnt3a deficiency irreversibly impairs hematopoietic stem cell self-renewal and leads to defects in progenitor cell differentiation." 2009, Blood. 113:546-554.
Malhotra, et al., "Wnt-related molecules and signaling pathway equilibrium in hematopoiesis." 2009, Cell Stem Cell. 4:27-36.
Phiel and Klein, et al., "Molecular targets of lithium action." 2001, Annu. Rev. Pharmacol. Toxicol. 41:789-813.
Reya, et al., "A role for Wnt signalling in self-renewal of haematopoietic stem cells." 2003, Nature. 423:409-414.
Reya, et al., "Wnt signalling in stem cells and cancer." 2005, Nature. 434:843-850.

(Continued)

*Primary Examiner* — Taeyoon Kim
(74) *Attorney, Agent, or Firm* — Riverside Law LLP

(57) ABSTRACT

The present invention provides a therapeutic approach to maintain and expand HSCs in vivo using currently available medications that target GSK-3 and mTOR. The present invention also provides a system and method for the ex vivo culturing of HSCs, where an mTOR inhibitor is combined with a GSK-3 inhibitor within the culturing conditions.

9 Claims, 21 Drawing Sheets

(56) References Cited

OTHER PUBLICATIONS

Ricci, et al. "Haematological effects of lithium carbonate: a study in 56 psychiatric patients." 1981, Haematologica. 66:627-633.

Sato, et al., "Maintenance of pluripotency in human and mouse embryonic stem cells through activation of Wnt signaling by a pharmacological GSK-3-specific inhibitor." 2004, Nat. Med. 10:55-63.

Scheller, et al., "Hematopoietic stem cell and multilineage defects generated by constitutive beta-catenin activation." 2006, Nat. Immunol. 7:1037-1047.

Staal, et al., "Tcf-1-mediated transcription in T lymphocytes: differential role for glycogen synthase kinase-3 in fibroblasts and T cells." 1999, Int. Immunol. 11:317-323.

Staal, et al., "The canonical Wnt signaling pathway plays an important role in lymphopoiesis and hematopoiesis." 2008, Eur. J. Immunol. 38:1788-1794.

Stambolic, et al., "Lithium inhibits glycogen synthase kinase-3 activity and mimics wingless signalling in intact cells." 1996, Curr. Biol. 6:1664-1668.

Trowbridge, et al., "Glycogen synthase kinase-3 is an in vivo regulator of hematopoietic stem cell repopulation." 2006. Nat. Med. 12:89-98.

Van Den Berg, et al., "Role of members of the Wnt gene family in human hematopoiesis." 1998, Blood. 92:3189-3202.

Willert, et al., "Wnt proteins are lipid-modified and can act as stem cell growth factors." 2003, Nature. 423:448-452.

Yilmaz, et al., "Pten dependence distinguishes haematopoietic stem cells from leukaemia-initiating cells." 2006, Nature. 441:475-482.

Ying, et al., "The ground state of embryonic stem cell self-renewal." 2008, Nature. 453:519-523.

Zhang, et al., "PTEN maintains haematopoietic stem cells and acts in lineage choice and leukaemia prevention." 2006, Nature. 441:518-522.

Zhao, et al., "Loss of beta-catenin impairs the renewal of normal and CML stem cells in vivo." 2007, Cancer Cell. 12:528-541.

* cited by examiner

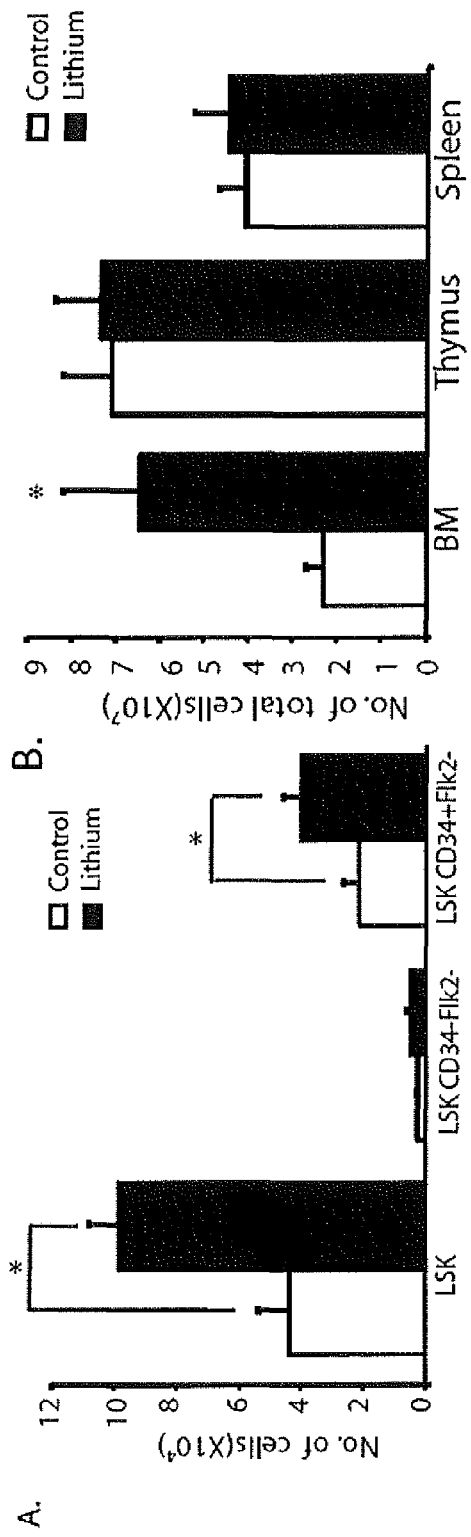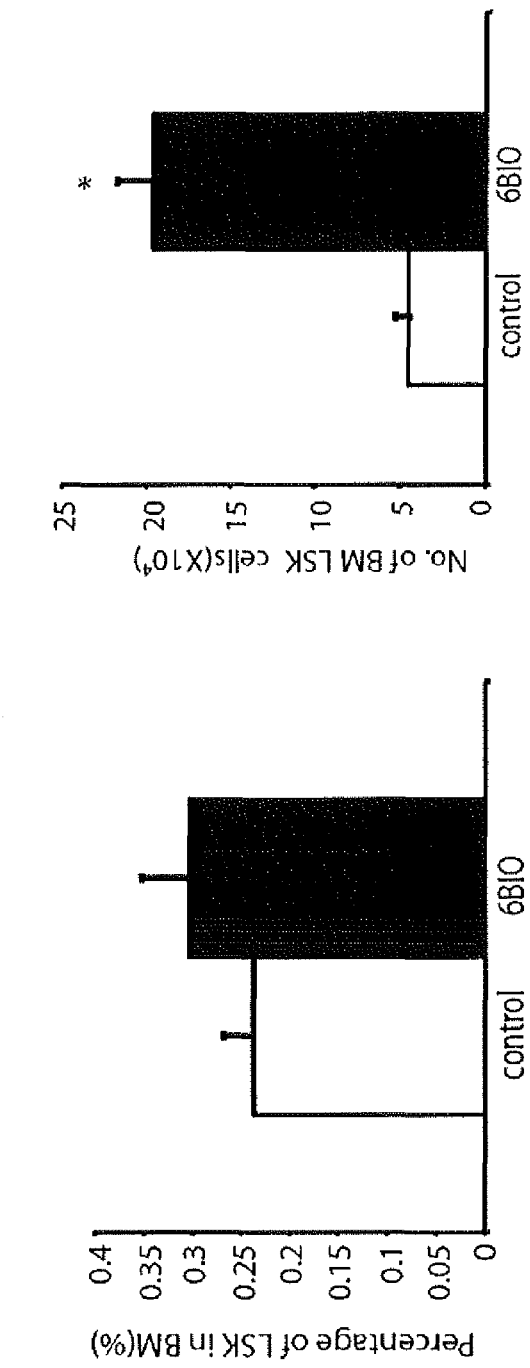
Figures 1A-1C

IN VIVO AND EX VIVO EXPANSION OF HEMATOPOIETIC STEM CELLS WITH A TARGETED COMBINATION OF CLINICALLY TESTED, FDA APPROVED DRUGS

CROSS REFERENCE TO RELATED APPLICATIONS

The present application is entitled to priority under 35 U.S.C. §119(e) to U.S. Provisional Application No. 61/323,203, filed Apr. 12, 2010, which application is hereby incorporated by reference herein in its entirety.

STATEMENT REGARDING FEDERALLY SPONSORED RESEARCH OR DEVELOPMENT

This invention was made with government support under R01MH58324 awarded by the National Institute of Health. The government has certain rights in the invention.

BACKGROUND OF THE INVENTION

It is well accepted that stem cells possess the unique ability to self renew and differentiate into a diverse range of specialized cell types. For example, hematopoietic stem cells (HSCs) have provided an important window into stem cell biology as well as a valuable clinical tool for treatment of hematopoietic malignancies and other disorders. However, the complex signaling network regulating the balance between HSC self renewal and differentiation is still not well understood.

One important regulator of HSC homeostasis is suggested by the highly prevalent clinical finding that therapeutic lithium increases circulating HSCs (as CD34+ cells; Bailin, et al., 1998. Br. J. Haematol. 100:219-221) and peripheral blood counts (Boggs, et al., 1983, Semin. Hematol. 20:129-138; Joyce, 1984, Br. J. Haematol. 56:307-321; Ricci, et al. 1981, Haematologica. 66:627-633) in greater than 90% of patients taking lithium, and the laboratory findings that lithium also increases transplantable HSCs in mice (Boggs, et al., 1983. Semin. Hematol. 20:129-138; Joyce, 1984, Br. J. Haematol. 56:307-321). Because lithium directly inhibits glycogen synthase kinase-3 (GSK-3) (GSK-3; Klein, et al., 1996, Proc. Natl. Acad. Sci. U.S.A. 93:8455-8459), activating critical signaling pathways such as the Writ and PI3K/PTEN/Akt pathways (Hedgepeth, et al., 1997, Dev. Biol. 185:82-91; Stambolic, et al., 1996, Curr. Biol. 6:1664-1668), these clinical and laboratory observations implicate GSK-3 as an important regulator of HSC homeostasis (Hedgepeth, et al., 1997, Dev. Biol. 185:82-91; Phiel, et al., 2001, Annu. Rev. Pharmacol, Toxicol. 41:789-813; Focosi, et al., 2009, J. Leukoc. Biol. 85:20-28). Support for this hypothesis comes from pharmacological studies showing that HSCs and hematopoietic progenitor cells (HPCs) are increased, and hematopoietic repopulation is enhanced when BM transplant recipient mice are treated with alternative GSK-3 inhibitors (Trowbridge, et al., 2006. Nat. Med. 12:89-98; Goessling, et al., 2009, Cell. 136:1136-1147; Holmes, et al., 2008, Stem Cells. 26:1288-1297). Furthermore, mouse ES cells treated with GSK-3 inhibitors maintain pluripotency (Sato, et al., 2004, Nat. Med. 10:55-63; Ying, et al., 2008, Nature. 453:519-523), and mouse ES cells lacking Gsk3a and Gsk3b maintain expression of markers of pluripotency under conditions that induce control ES cells to differentiate (Doble, et al., 2007, Dev. Cell, 12:957-971). These observations suggest a negative role for GSK-3 in ESC renewal. However, Gsk-3 loss of function in HSCs has not previously been performed, and the downstream pathways regulated by GSK-3 in HSCs have not yet been established.

Canonical Wnt signaling, which inhibits GSK-3 and thereby stabilizes beta-catenin, plays a central role in the self renewal of diverse stem cell populations (Sato, et al., 2004, Nat. Med. 10:55-63; Doble, et al., 2007, Dev. Cell. 12:957-971; Staal, et al., 1999, Int. Immunol. 11:317-323; Reya, et al., 2005, Nature. 434:843-850; Staal, et al., 2008, Eur. J. Immunol. 38:1788-1794; Malhotra, et al., 2009, Cell Stem Cell, 4:27-36). A role for Wnt signaling in hematopoiesis is supported by observations that Wnt ligands enhance proliferation of HSCs ex vivo (Austin, et al., 1997, Blood. 89:3624-3635; Van Den Berg, et al., 1998, Blood. 92:3189-3202; Willert, et al., 2003, Nature. 423:448-452) and that Wnt antagonists inhibit HSC proliferation and reconstitution (Reya, et al., 2003, Nature. 423:409-414; Jeannet, et al., 2008, Blood. 111:142-149). In addition, overexpression of stabilized β-catenin promotes HSC self renewal and proliferation ex vivo under certain conditions (Austin, et al., 1997, Blood. 89:3624-3635; Van Den Berg, et al., 1998, Blood. 92:3189-3202; Willert, et al., 2003, Nature, 423:448-452; Reya, et al., 2003, Nature. 423:409-414; Baba, et al., 2006, J. Immunol. 177:2294-2303), and conditional deletion of β-catenin using vav-cre impairs HSC function in competitive repopulation assays (Zhao, et al., 2007, Cancer Cell. 12:528-541). Furthermore, long-term reconstituting capacity in serial transplants is impaired in HSCs recovered from fetal liver of Wnt3a KO embryos (Austin, et al., 1997, Blood, 89:3624-3635; Van Den Berg, et al., 1998, Blood. 92:3189-3202; Willert, et al., 2003, Nature. 423:448-452; Reya, et al., 2003, Nature. 423:409-414; Baba, et al., 2006, J. Immunol. 177:2294-2303; Luis, et al., 2009, Blood. 113:546-554) or from adults overexpressing the Wnt inhibitor Dkk in the hematopoietic niche (Fleming, et al., 2008, Cell Stem Cell. 2:274-283), which suggests that Wnt signaling is required to maintain the long-term repopulating activity of HSCs.

However, there are conflicting reports on the requirement for Wnt/β-catenin signaling in basal hematopoiesis: conditional disruption of β-catenin and γ-catenin/plakoglobin in adult HSCs does not affect their ability to self renew and reconstitute hematopoietic lineages (Jeannet, et al., 2008, Blood. 111:142-149; Cobas, et al., 2004, J. Exp. Med. 199:221-229; Koch, et al., 2008, Blood. 111:160-164). In addition, although overexpression of stabilized β-catenin increases immunophenotypic HSCs, this is associated with a loss of repopulating activity and hematopoietic failure in vivo (Scheller, et al., 2006, Nat. Immunol. 7:1037-1047; Kirstetter et al., 2006, Nat. Immunol. 7:1048-1056), findings that appear incompatible with a positive role for β-catenin in hematopoiesis. A general conclusion from these apparently conflicting reports is that the role of Wnt signaling in hematopoiesis is complex and context dependent (Staal, et al., 2008, Eur. J. Immunol. 38:1788-1794; Malhotra, et al., 2009, Cell Stem Cell. 4:27-36). However, although the β-catenin loss-of-function studies suggest that canonical Wnt signaling is not essential for basal hematopoiesis in adults, they do not rule out a possible role for the Wnt/β-catenin pathway under nonbasal conditions, and are still compatible with gain-of-function experiments in which the pathway is activated.

GSK-3 is also inhibited by Akt/PKB, which in turn requires the activity of PI3K and is antagonized by phosphatase and tensin homolog (PTEN), a PI3 phosphatase. Loss of Pt en transiently increases HSCs, which is followed by progressive HSC depletion, increased lineage commitment resembling myeloproliferative disorder, and acute leukemia (Yilmaz, et al., 2006, Nature. 441:475-482; Zhang, et al., 2006, Nature.

441:518-522). This expansion and subsequent depletion in Pten KO HSCs is mediated through mammalian target of rapamycin (mTOR), as the phenotype is reversed by treatment with rapamycin (Yilmaz, et al. 2006, Nature. 441:475-482), and a similar HSC phenotype is observed with KO of tuberous sclerosis complex 1 (Tsc1), a negative regulator of mTOR (Chen, et al., 2008, J. Exp. Med. 205:2397-2408; Gan, et al., 2008, Proc. Natl. Acad. Sci. U.S.A. 105:19384-19389). As GSK-3 is an indirect target of PTEN and antagonizes mTOR through phosphorylation of Tsc2 (Inoki, et al., 2006, Cell. 126:955-968), inhibition of GSK-3 could mimic the hematopoietic phenotype of Pten and Tsc1 KOs.

Currently available pharmacological data from humans and mice suggest that GSK-3 is an important regulator of HSC homeostasis, but the pathways regulated by GSK-3 in HSCs have not been defined. Furthermore, Gsk-3 loss of function in HSCs/HPCs has not previously been reported for either Gsk3a or Gsk3b, and this is an essential step to defining the role of Gsk-3 within HSCs.

Without question, the maintenance and expansion of long-term transplantable HSCs under in vivo and ex vivo conditions is a crucial component and major challenge in stem cell research and therapeutic hematopoietic stem cell transplantation. Thus, the ability to maintain and expand HSCs in culture has long been deemed the holy grail of hematopoietic stem cell research. Unfortunately, the ability to expand HSCs consistently and effectively in ex vivo culture conditions has not yet been perfected. Therefore, there is a long felt need in the art for a culturing system and method for maintaining and expanding HSCs. By understanding the complex signaling network regulating the balance between HSC self renewal and differentiation, the present invention satisfies this need.

BRIEF SUMMARY OF THE INVENTION

The invention includes a method for the maintenance and expansion of a hematopoietic stem cell (HSC). The method includes culturing the HSC in a medium including at least one glycogen synthase kinase-3 (GSK-3) inhibitor and at least one mammalian target of rapamycin (mTOR) inhibitor, wherein the multipotentiality of the HSC is retained during the culturing.

In one embodiment, the HSC is derived from a mammal. In another embodiment, the mammal is a human. In yet another embodiment, exogenous genetic material is introduced into the HSC. In yet another embodiment, the medium further includes at least one cytokine. In yet another embodiment, the medium further includes a promotion factor. In yet another embodiment, the GSK-3 inhibitor is lithium, or a salt thereof. In yet another embodiment, the mTOR inhibitor is rapamycin. In yet another embodiment, the culturing is ex vivo.

The invention also includes an isolated HSC prepared by a method of culturing the HSC in a medium comprising at least one GSK-3 inhibitor and at least one mTOR inhibitor, wherein the multipotentiality of the isolated HSC is retained during the culturing.

The invention further includes a method of treating a mammal having a disease, disorder or condition. The method includes obtaining an isolated HSC from a donor, culturing the HSC in a medium comprising at least one GSK-3 inhibitor and at least one mTOR inhibitor, and administering the cultured HSC to the mammal.

In one embodiment, the mammal is a human. In another embodiment, the isolated HSC is allogeneic with respect to the mammal. In yet another embodiment, the isolated HSC is autologous with respect to the mammal. In yet another embodiment, the disease, disorder or condition is selected from the group consisting of a genetic disease, acute lymphoblastic leukemia, acute myeloblastic leukemia, chronic myelogenous leukemia (CML), Hodgkin's disease, multiple myeloma, non-Hodgkin's lymphoma, anemia, aplastic anemia, beta-thalassemia, Blackfan-Diamond syndrome, globoid cell leukodystrophy, sickle-cell anemia, severe combined immunodeficiency, X-linked lymphoproliferative syndrome, Wiskott-Aldrich syndrome, Hunter's syndrome, Hurler's syndrome, Lesch Nyhan syndrome, and osteopetrosis. In yet another embodiment, the cultured HSC administered to the mammal remains present and/or replicates in the mammal. In yet another embodiment, prior to administering the HSC, the HSC is cultured ex vivo in the medium. In yet another embodiment, prior to administering the HSC, the HSC is genetically modified.

The invention further includes a culturing medium for expanding and maintaining HSC. The culturing medium includes at least one GSK-3 inhibitor and at least one mTOR inhibitor, wherein the multipotentiality of the HSC is retained while the HSC is maintained or expanded in the culturing medium.

The invention further includes a method for the in vivo maintenance and expansion of HSC in a mammal. The method includes transplanting the HSC into a tissue of the mammal and administering to the mammal at least one GSK-3 inhibitor and at least one mTOR inhibitor.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising FIG. 1A-1E, demonstrates that lithium and other GSK-3 inhibitors expand HSC/HPCs. FIG. 1A depicts the absolute number of Lineage-Sca-1+cKit+ (LSK) fraction, which is enriched for HSCs, and immunophenotypic LT-HSC (LSK; CD34-Flk2-) and ST-HSC (LSK CD34+Flk-2-) fractions in bone marrow harvested from mice treated with control or lithium diet for 2 weeks. FIG. 1B depicts the cellularity of bone marrow, thymus and spleen in control and lithium treated mice, shown as the number of nucleated cells/mouse recovered from both femurs and tibias, thymus, and spleen. FIG. 1C depicts the percentage (left) and absolute number (right) of HSC/HPCs (as LSK) in mice treated with 6BIO vs control for two weeks.

FIG. 2, comprising FIGS. 2A-2H, demonstrates that Gsk-3 depletion expands HSCs and HPCs in primary bone marrow (BM) transplants. As depicted in FIG. 2A, irradiated mice were reconstituted with BM after transduction with lentivirus with or without Gsk3-rnai. Peripheral blood was examined 20 weeks after transplantation, where numbers within histograms indicate percent GFP$^+$ cells. One representative of five similar experiments is illustrated, and similar results were obtained with Gsk3-rnai-C4.

FIG. 3, comprising FIG. 3A depicts a flow cytometric detection of Annexin V using bone marrow cells harvested from 1° recipients after 4 month bone marrow transplantation from both control and Gsk3 RNAi. Annexin V was measured in the GFP+LSK gated population. FIG. 3B depicts the total number of bone marrow cells and number of GFP+ cells recovered in bone marrow from 1° recipients after 4 month transplant. FIG. 3C depicts the total number and number of GFP+ cells recovered in bone marrow from 2° recipients after 4 months. FIG. 3D depicts the total number and number of GFP+ cells recovered in bone marrow from 3° recipients after 4 months.

FIG. 4, comprising FIGS. 4A and 4B, demonstrates that Gsk-3 knockdown increases cycling of the HSC-enriched LSK cell population. To assess cell cycle status of the HSC-enriched LSK population, sorted GFP$^+$ LSK and GFP$^+$ LSK Flk2$^-$ cells from primary recipients of control and Gsk3-rnai 4 months after BM transplantation were stained with Hoechst and Pyronin and analyzed by FCM, as depicted in FIG. 4A. Representative FACS data are shown for control versus Gsk3-rnai-C2. As depicted in FIG. 4B, at 4 months after BM transplantation, primary recipients of control and Gsk3-rnai were fed BrdU in the drinking water for 7 days. Sorted GFP$^+$ LSK Flk2$^+$ and Flk2$^-$ cells were stained with BrdU-APC antibody and PI to analyze BrdU incorporation. Representative FACS data are shown for control versus Gsk3-rnai-C2. Similar results were obtained by BrdU versus 7-AAD staining (BD). Percent cells are shown for the indicated gates and quadrants.

FIG. 6, comprising FIGS. 6A-6H, demonstrates that Gsk-3 knockdown depletes HSCs in serial BM transplants. As depicted in FIG. 6A, noncompetitive serial transplants were performed by transplanting 2×10$^5$ sorted GFP$^+$ cells from primary recipients of control or Gsk3-rnai transduced BM into lethally irradiated recipients (10 mice per group). Survival of secondary recipients receiving control or Gsk3-rnai BM is shown as a Kaplan-Meier plot.

FIGS. 8A and 8B, depicts increased colony formation induced by Gsk3-rnai requires β-catenin. A colony formation assay was performed using sorted GFP+ cells harvested from 1° recipients (FIG. 8A) or 2° recipients (FIG. 8B) of wild-type (left) and β-catenin KO (right) marrow transduced with control (open boxes) or Gsk3-rnai (filled boxes) lentivirus. Data represent mean number of colonies per well for five mice per construct repeated in three separate experiments.

FIG. 9, comprising FIGS. 9A-9H, demonstrates increased HSCs/HPCs in rapamycin-treated recipients of Gsk3-depleted BM and increased survival of tertiary recipients receiving Gsk3-depleted BM from rapamycin treated 2° hosts. As depicted in FIG. 9A, BM was harvested from Mx-Cre; β-catenine$^{fl/fl}$ mice treated with or without polyI:polyC, transduced with control or Gsk3-rnai lentivirus, and transplanted into irradiated recipients. After 4 months, GFP$^+$ cells were sorted (pooled from 5 mice per group), and phospho-ribosomal protein S6 (p-S6) was detected in cell lysates by immunoblot.

FIGS. 10A and 10B depict reconstitution of peripheral blood, including B cells (B220$^+$), T cells (CD3$^+$), and myeloid cells (Mac-1$^+$GR-1$^+$), in primary (FIG. 10A) and secondary (FIG. 10B) recipients of WT, Gsk3b$^{+/-}$, and Gsk3b$^{-/-}$ fetal liver cells. Secondary transplants were performed after 16 weeks of engraftment by pooling BM from 3-4 reconstituted primary recipients to transplant $4 \times 10^5$ whole BM cells into lethally irradiated CD45.1 secondary recipients (10 hosts per genotype). As depicted in FIGS. 10C and 10D, percentage of LSK cells in CD45.2$^+$BM was compared among recipients of WT, Gsk3b$^{+/-}$, and Gsk3b$^{-/-}$ fetal liver cells in primary (FIG. 10C) and secondary (FIG. 10D) hosts. *P<0.05.

DETAILED DESCRIPTION

Figures 1D, 1E:
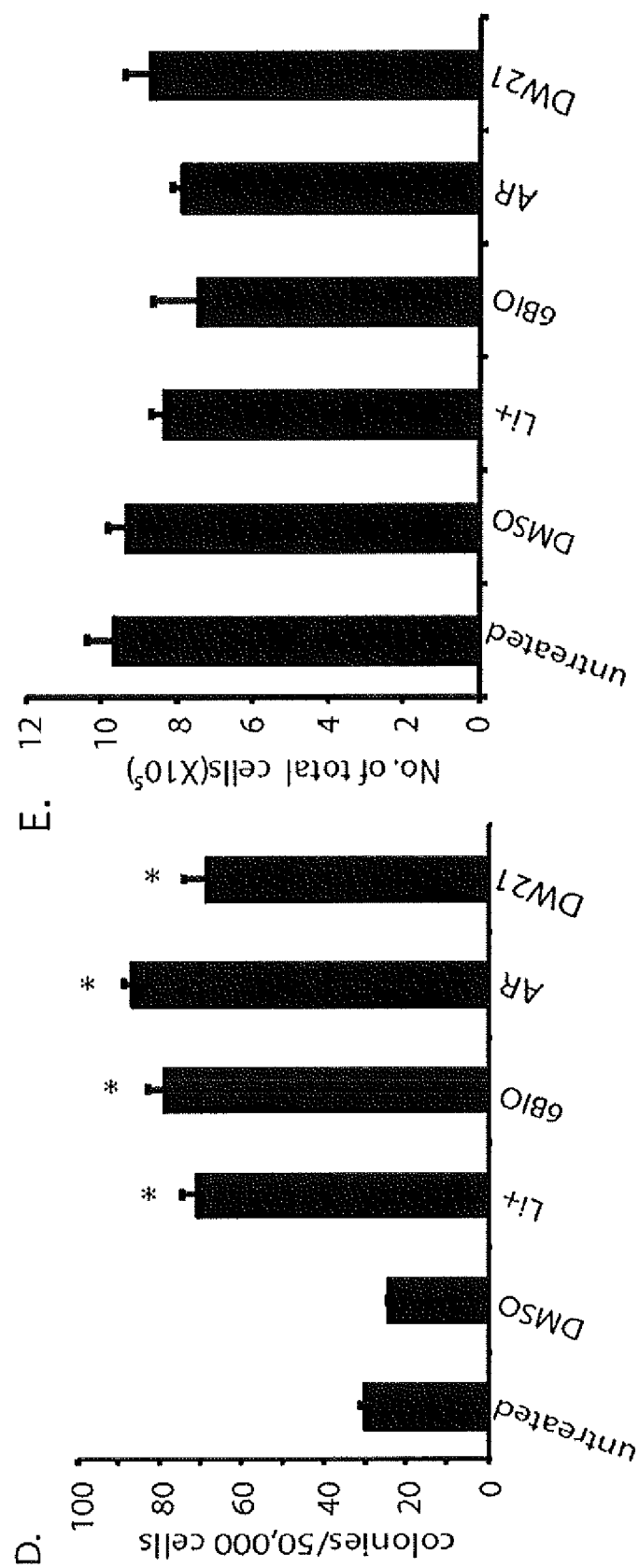
FIG. 1D depicts a colony formation assay: Purified total c-Kit+ cells were treated with lithium, 6BIO, AR-A014418, or Ru (1-OH) (also known as DW12) for 3 days and plated in methylcellulose with hematopoietic cytokines for 12 days. Colonies of >30 viable cells were counted and the mean colony number/50,000 plated cells for each of three separate experiments is shown.
FIG. 1E depicts the total numbers of c-Kit+ cells in each drug treatment after 3 days. The primary cultures are shown.

The present invention provides a therapeutic approach to expand HSCs in vivo using currently available medications that target GSK-3 and mTOR. The present invention also provides a system and method for the ex vivo culturing of HSCs, where an mTOR inhibitor is combined with a GSK-3 inhibitor within the culturing conditions. The present invention is based on the discovery that Gsk-3 loss of function coupled with inhibition of mTOR provides for improved maintenance and expansion of HSCs in vivo and ex vivo. It is demonstrated herein that knockdown of Gsk-3a/b (hereafter, Gsk-3 is used to refer to both genes) initially expand the HSC-enriched pool of lineage$^-$sca-1$^+$c-kit$^+$ (LSK) cells, similar to the effects of lithium and other GSK-3 inhibitors, and this requires endogenous β-catenin function. However, in assays of long-term stem cell function, Gsk3-deficient HSCs are progressively depleted, revealing an unexpected positive role for GSK-3 in the maintenance of HSC self renewal. Furthermore, the data suggest that GSK-3 functions downstream of PTEN to antagonize mTOR signaling in phenotypic HSCs (HSC-enriched LSK population) in addition to its role in antagonizing Wnt/β-catenin signaling. Based on these observations, Gsk-3 loss of function coupled with inhibition of mTOR expands phenotypic HSCs in vivo. These findings point to a critical role for GSK-3 in regulating the decision between self renewal and differentiation in HSCs.

DEFINITIONS

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

"Allogeneic" refers to a graft derived from a different animal of the same species. As used herein, the term "autologous" is meant to refer to any material derived from the same individual to which it is re-introduced.

The terms "precursor cell," "progenitor cell," and "stem cell" are used interchangeably in the art and herein and refer either to a pluripotent, or lineage-uncommitted, progenitor cell, which is potentially capable of an unlimited number of mitotic divisions to either renew itself or to produce progeny cells which will differentiate into the desired cell type. Unlike pluripotent stem cells, lineage-committed progenitor cells are generally considered to be incapable of giving rise to numerous cell types that phenotypically differ from each other. Instead, progenitor cells give rise to one or possibly two lineage-committed cell types.

As used herein, a "substantially purified" cell is a cell that is essentially free of other cell types. Thus, a substantially purified cell refers to a cell which has been purified from other cell types with which it is normally associated in its naturally occurring state.

"Transplant" refers to a biocompatible lattice or a donor tissue, organ or cell, to be transplanted. An example of a transplant may include but is not limited to a tissue, a stem cell, a neural stem cell, a skin cell, bone marrow, and solid organs such as heart, pancreas, kidney, lung and liver.

As used herein, a "therapeutically effective amount" is the amount of a therapeutic composition, such as a GSK-3 and/or mTOR inhibitor, sufficient to provide a beneficial effect to a mammal or culture or culturing system to which the composition is administered.

As used herein "endogenous" refers to any material from or produced inside an organism, cell or system.

"Exogenous" refers to any material introduced from or produced outside an organism, cell, or system.

"Expandability" is used herein to refer to the capacity of a cell to proliferate for example to expand in number, or in the case of a cell population, to undergo population doublings.

"Graft" refers to a cell, tissue, organ or otherwise any biological compatible lattice for transplantation.

As used herein, the term "growth medium" is meant to refer to a culture medium that promotes growth of cells.

As used herein, the term "modulate" is meant to refer to any change in biological state, i.e. increasing, decreasing, and the like.

"Proliferation" is used herein to refer to the reproduction or multiplication of similar forms, especially of cells. That is, proliferation encompasses production of a greater number of cells, and can be measured by, among other things, simply counting the numbers of cells, measuring incorporation of $^3$H-thymidine into the cells, and the like.

As used herein, a "promotion factor" refers to any molecule that assists in maintaining and/or proliferating cells.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains components such as, without limitation, a nucleic acid, peptide, cells, one or more inhibitors and/or composition of the invention or be shipped together with a container which contains such components. Alternatively, the instructional material may be shipped separately from the container with the intention that the instructional material and the components be used cooperatively by the recipient.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Hematopoietic stem cell (HSC) homeostasis depends on the balance between self renewal and lineage commitment, but what regulates this decision is not well understood. Using loss-of-function approaches in mice, it is demonstrated herein that glycogen synthase kinase-3 (Gsk-3) plays a pivotal role in controlling the decision between self renewal and differentiation of HSCs. Disruption of Gsk-3 in bone marrow (BM) transiently expanded phenotypic HSCs in a β-catenin-dependent manner, consistent with a role for Wnt signaling in HSC homeostasis. However, in assays of long-term HSC function, disruption of Gsk-3 progressively depleted HSCs through activation of the mammalian target of rapamycin (mTOR). This long-term HSC depletion was prevented by mTOR inhibition, and exacerbated by β-catenin knockout. Thus, the present invention is based on the discovery that GSK-3 regulates both Wnt and mTOR signaling in mouse HSCs, where these pathways promote HSC self renewal and lineage commitment, respectively, such that inhibition of Gsk-3 in the presence of rapamycin expands the HSC pool in vivo. Therefore, the present invention provides a therapeutic approach to expand HSCs in vivo using currently available medications that target GSK-3 and mTOR, and provides a compelling explanation for the clinically prevalent hematopoietic effects observed in individuals prescribed the GSK-3 inhibitor lithium.

The present invention also provides a system and method for the ex vivo culturing of HSCs, where an mTOR inhibitor is combined with a GSK-3 inhibitor within the culturing conditions. By simultaneously inhibiting GSK-3 and mTOR, HSCs can survive and increase in number within ex vivo culturing conditions. As contemplated herein, the present invention may also allow for expansion of human umbilical cord blood HSCs or adult donor HSCs, and improve the frequency of engraftment and shortened the time to hematopoietic recovery in recipient bone marrow transplant patients.

The advantage of cord blood is that this can be transplanted with markedly reduced risk of graft versus host disease and the potential for reduced immunosuppressive therapy of bone marrow transplant recipients. The present invention also bypasses the need for expensive cytokines to diminish the potential side effects associated with introducing foreign DNA into bone marrow cells. As contemplated herein, treatment may include ex vivo culture or included in the treatment regiment for transplant recipients.

Source of HSC

The classic source of HSCs is bone marrow (BM). In an embodiment of the present invention, HSCs may be harvested from BM. BM cells may be collected by puncturing a bone and flushing out the bone marrow cells with a syringe. About 1 in every 100,000 cells in the marrow is a long-term, blood-forming stem cell. Other cells present include stromal cells, stromal stem cells, blood progenitor cells, and mature and maturing white and red blood cells.

In another embodiment, donor cells may be harvested from peripheral, circulating blood. While a small number of stem and progenitor cells circulate in the bloodstream, improved cell counts may be obtained by injecting the donor with a cytokine, such as granulocyte-colony stimulating factor (GCSF). The donor is injected with GCSF a few days before the cell harvest. To collect the cells, an intravenous tube is inserted into the donor's vein and the blood is passed through a filtering system that extracts out $CD34^+$ white blood cells and returns the red blood cells to the donor. Of the $CD34^+$ cells collected, approximately 5 to 20 percent may be HSCs, where the remaining cells are a mixture of stem cells, progenitors, and white blood cells of varying degrees of maturity.

In other embodiments, blood from the human umbilical cord and placenta may be collected and used as a rich source of HSCs. In still other embodiments, developing blood-producing tissues of fetal animals may provide a source of HSCs for research purposes, as hematopoietic cells appear early in the development of all vertebrates. As contemplated herein, the there is no limitation to the source of HSCs, the manner in which they are harvested, or the timing of such harvesting.

HSC Culturing Conditions

According to an aspect of the present invention, an ex vivo culture system and process for the maintenance and expansion HSCs is provided, such that the expanded cells can be engrafted into patients without losing their capability for multilineage differentiation and reconstitution. HSCs have the capability of both self-renewal and the ability to differentiate into distinct hematopoietic cell lineages, such as myeloid, B-cell and T-cell lineages. As contemplated herein, the ex vivo maintenance and expansion of HSCs can be achieved by culturing HSCs in the presence of GSK-3 and mTOR inhibitors.

In one embodiment of the present invention, mammalian HSCs, preferably human HSCs, can be expanded ex vivo by culturing isolated HSCs in a culture medium which comprises the combination of at least one GSK-3 inhibitor and at least one mTOR inhibitor. In addition to the at least one GSK-3 inhibitor and at least one mTOR inhibitor, the culture medium further comprises any culture medium suitable for culturing HSCs. In some embodiments, the culturing medium may include serum, while in other embodiments, the culturing medium may be serum-free. Standard culture media for HSCs typically contains a variety of essential components required for cell viability, including inorganic salts, carbohydrates, hormones, essential amino acids, vitamins, and the like. Preferably, the conditions for culturing the HSCs should be as close to physiological conditions as possible. The culturing medium, as contemplated herein, may include components that are known to those of ordinary skill in the art and may comprise such components as RPMI 1640, HEPES, FCS, and common antibiotics. Any commercially available HSC culturing medium may be used, such as X-VIVO™ medium, such that the GSK-3 inhibitor and the mTOR inhibitor may be added to the commercially available HSC culturing medium in effective amounts as contemplated and described hereinthroughout.

As explained above, isolated HSC are cultured in a culture system which comprises a culture medium containing the GSK-3 inhibitor and the mTOR inhibitor. Such a culture system is suitable for achieving an expansion, such as about a 1-fold expansion, a 2-fold expansion, a 3-fold expansion, a 4-fold expansion, a 5-fold expansion, a 10-fold expansion, a 20-fold expansion, a 50-fold expansion, a 100-fold expansion, a 150-fold expansion, or a 200-fold expansion or more and any and all whole or partial increments there between of the HSCs. The expanded HSCs may retain their capability for multilineage differentiation upon introduction into the body of a patient, preferably a human patient.

HSCs can be cultured in the presence of the at least one GSK-3 inhibitor and at least one mTOR inhibitor for approximately 7 days. Alternatively, the HSCs can be cultured in the presence of at least one GSK-3 inhibitor and at least one mTOR inhibitor for approximately 14 days, approximately 28 days, approximately 60 days or approximately 120 days or more, and any and all whole and partial increments there between.

GSK-3 and mTOR Inhibitors

GSK-3 is involved in many cellular and physiological events, including Wnt and Hedgehog signaling, transcription, insulin action, cell-division cycle, response to DNA damage, cell death, cell survival, patterning and axial orientation during development, differentiation, neuronal functions, circadian rhythm and others. In humans, two genes, which map to 19q13.2 and 3q13.3, encode two distinct but closely related GSK-3 forms, GSK-3a (51 kDa) and GSK-3b (47 kDa).

GSK-3 is regulated at multiple levels. First, GSK-3b is regulated by post-translational phosphorylation of Ser9 (inhibitory) and Tyr216 (activating) (Ser21 and Tyr279, respectively, in GSK-3a). Phosphorylated Ser9 in the N-terminal domain of GSK-3b acts as a pseudo-substrate that blocks the access of substrates to the catalytic site. Unphosphorylated Tyr216 in the T-loop domain prevents access of substrates to the catalytic site, and phosphorylation releases this inhibition. Second, GSK-3b is regulated by interactions with many other proteins. Axin and presenilin act as docking proteins that allow the substrates to make contact with the priming kinase [casein kinase (CK1) and protein kinase A, respectively] and GSK-3. Docking proteins might, thus, specify different GSK-3 functions in the cell. Third, GSK-3 action requires the priming phosphorylation of its substrates by another kinase on a serine residue located four amino acids C-terminal to the GSK-3 phosphorylation site. Fourth, GSK-3 is regulated through its intracellular distribution.

In one exemplary embodiment, lithium, such as in the form of LiCl, may be used as an inhibitor of GSK-3. As contemplated herein, any other GSK-3 inhibitor in any form may be used, either separately or in combination, as would be understood by those skilled in the art, provided such inhibitors do not orientate the differentiation of the HSCs into well-defined, committed cell lineages, unless such a result is desired. Other such GSK-3 inhibitors may include, without limitation, 6BIO, CHIR-911, DW21, AR-A014418, TDZD and their related compounds.

mTOR is a kinase protein predominantly found in the cytoplasm of the cell. It acts as a central regulator of many biological processes that are essential for cell proliferation, angiogenesis, and cell metabolism. mTOR exerts its effects primarily by turning on the cell's translational machinery, and is therefore responsible for protein synthesis. mTOR is a key intracellular point of convergence for a number of cellular signaling pathways.

In one exemplary embodiment, rapamycin, which is also known as sirolimus, may be used as an mTOR inhibitor. To inhibit mTOR, rapamycin binds to an abundant intracellular binding protein, FKBP-12, and the dntg:FKPB-12 complex binds at the rapamycin binding domain. In another embodiment, temsirolimus, which is also known as CCI-779, may be used as an mTOR inhibitor. In another embodiment, everolimus, which is also known as RAD001, may be used as an mTOR inhibitor. Everolimus and temsirolimus are considered rapamycin derivatives, the primary difference being their pharmacokinetic and pharmacologic properties. Temsirolimus was created by adding an ester to a rapamycin carbon, and adding an ether created everolimus. As contemplated herein, any other mTOR inhibitor in any form may be used, either separately or in combination, as would be understood by those skilled in the art.

As contemplated herein, an effective amount of each inhibitor is added to the culturing medium. The actual amount of inhibitor added to the culturing medium can vary according to the culturing volume, additional culturing components, and the particular inhibitor selected. For example, about 5 mM LiCl and about 5 nM rapamycin may be an effective amount of each inhibitor, and added to X-VIVO15 medium for culturing in multi-well plates.

Additional Culturing Components

In an alternative embodiment of the present invention, the culture medium may include at least one cytokine. However, it should be appreciated that the present invention does not require the inclusion of a cytokine, and thus the addition of at least one cytokine is optional. Without limitation, such cytokines may include interleukins 3 and 6 (Il-3 and Il-6), stem cell factor (SCF), granulocyte-macrophage colony stimulating factor (GM-CSF), Flt-3 ligand (FL), and thrombopoietin (TPO). A single cytokine can be added or a combination of two or more cytokines can be added to the culture system. For example, the medium can include Il-3 or Il-6, or a combination thereof, or it may include TPO or CSF or a combination thereof. It is believed that the addition of at least one cytokine can enhance the expansion of HSC by at least about 50%, preferably at least about 100%.

In another alternative embodiment of the present invention, the culture medium may include at least one stem cell expansion promoting factor which is distinct from the aforementioned cytokines. For example, HSCs can be maintained and expanded ex vivo in the presence of stromal cell medium containing such promotion factors, such as a culture medium collected from cultured murine stromal cells where the stromal cells were cultured in the presence of a leukemia inhibitory factor.

Characterization

At any time point during the culturing of the cells with at least one GSK-3 inhibitor and at least one mTOR inhibitor, the cells can be harvested and collected for immediate experimental or therapeutic use, or cryopreserved for use at a later time. HSCs, as described herein, may be cryopreserved according to routine procedures. Preferably, about one to ten million cells are cryopreserved in medium with about 10% DMSO in vapor phase of Liquid $N_2$. Frozen cells can be thawed by swirling in a 37° C. bath, resuspended in fresh proliferation medium, and grown as usual. Cryopreservation is a procedure common in the art and as used herein encompasses all procedures currently used to cryopreserve cells for future analysis and use.

In another aspect, the cells can be harvested and subjected to flow cytometry to evaluate cell surface markers to assess the change in phenotype of the cells in view of the culture conditions. HSCs may be characterized using any one of numerous methods in the art and methods disclosed herein. The cells may be characterized by the identification of surface and intracellular proteins, genes, and/or other markers indicative of the cells.

Genetic Modification

The cells of the present invention can also be used to express a foreign protein or molecule for a therapeutic purpose or for a method of tracking their integration and differentiation in a patient's tissue. Thus, the invention encompasses expression vectors and methods for the introduction of exogenous DNA into the cells with concomitant expression of the exogenous DNA in the cells such as those described, for example, in Sambrook et al. (2001, Molecular Cloning: A Laboratory Manual, Cold Spring Harbor Laboratory, New York), and in Ausubel et al. (1997, Current Protocols in Molecular Biology, John Wiley & Sons, New York).

The isolated nucleic acid can encode a molecule used to track the migration, integration, and survival of HSCs once they are placed in the patient, or they can be used to express a protein that is mutated, deficient, or otherwise dysfunctional in the patient. Proteins for tracking can include, but are not limited to green fluorescent protein (GFP), any of the other fluorescent proteins (i.e., enhanced green, cyan, yellow, blue and red fluorescent proteins; Clontech, Palo Alto, Calif.), or other tag proteins (i.e., LacZ, FLAG-tag, Myc, $His_6$, and the like) disclosed elsewhere herein.

The present invention is also useful for obtaining HSCs that express an exogenous gene, so that the HSCs can be used, for example, for cell therapy or gene therapy. That is, the present invention allows for the production of large numbers of HSCs that express an exogenous gene. The exogenous gene can, for example, be an exogenous version of an endogenous gene (i.e., a wild type version of the same gene can be used to replace a defective allele comprising a mutation). The exogenous gene is usually, but not necessarily, covalently linked with (i.e., "fused with") one or more additional genes. Exemplary "additional" genes include a gene used for "positive" selection to select cells that have incorporated the exogenous gene, and a gene used for "negative" selection to select cells that have incorporated the exogenous gene into the same chromosomal locus as the endogenous gene or both.

An HSC expressing a desired exogenous gene can be used to provide the product of the exogenous gene to a cell, tissue, or whole mammal where a higher level of the gene product can be useful to treat or alleviate a disease, disorder or condition associated with abnormal expression, and/or activity. Therefore, the invention includes an HSC expressing an exogenous gene where increasing expression, protein level, and/or activity of the desired gene product can be useful to treat or alleviate a disease, disorder or condition.

According to the present invention, gene constructs which comprise nucleotide sequences that encode heterologous proteins are introduced into the HSCs. That is, the cells are genetically modified to introduce a gene whose expression has therapeutic effect in the individual. According to some aspects of the invention, HSCs from the individual to be treated or from another individual, or from a non-human animal, may be genetically modified to replace a defective gene and/or to introduce a gene whose expression has therapeutic effect in the individual being treated.

The term "genetic modification" as used herein refers to the stable or transient alteration of the genotype of an HSC by intentional introduction of exogenous DNA. DNA may be synthetic, or naturally derived, and may contain genes, portions of genes, or other useful DNA sequences. The term "genetic modification" as used herein is not meant to include naturally occurring alterations such as that which occurs through natural viral activity, natural genetic recombination, or the like.

Exogenous DNA may be introduced to an NSC using viral vectors (retrovirus, modified herpes viral, herpes-viral, adenovirus, adeno-associated virus, lentiviral, and the like) or by direct DNA transfection (lipofection, calcium phosphate transfection, DEAE-dextran, electroporation, and the like). The genetically modified cells of the present invention possess the added advantage of having the capacity to produce differentiated cells in a reproducible fashion using a number of differentiation protocols.

In all cases in which a gene construct is transfected into a cell, the heterologous gene is operably linked to regulatory sequences required to achieve expression of the gene in the cell. Such regulatory sequences typically include a promoter and a polyadenylation signal.

The gene construct is preferably provided as an expression vector that includes the coding sequence for a heterologous protein operably linked to essential regulatory sequences such that when the vector is transfected into the cell, the coding sequence will be expressed by the cell. The coding sequence is operably linked to the regulatory elements necessary for expression of that sequence in the cells. The nucleotide sequence that encodes the protein may be cDNA, genomic DNA, synthesized DNA or a hybrid thereof or an RNA molecule such as mRNA.

The gene construct includes the nucleotide sequence encoding the beneficial protein operably linked to the regulatory elements and may remain present in the cell as a functioning cytoplasmic molecule, a functioning episomal molecule or it may integrate into the cell's chromosomal DNA. Exogenous genetic material may be introduced into cells where it remains as separate genetic material in the form of a plasmid. Alternatively, linear DNA which can integrate into the chromosome may be introduced into the cell. When introducing DNA into the cell, reagents which promote DNA integration into chromosomes may be added. DNA sequences which are useful to promote integration may also be included in the DNA molecule. Alternatively, RNA may be introduced into the cell.

The regulatory elements for gene expression include: a promoter, an initiation codon, a stop codon, and a polyadenylation signal. It is preferred that these elements be operable in the cells of the present invention. Moreover, it is preferred that these elements be operably linked to the nucleotide sequence that encodes the protein such that the nucleotide sequence can be expressed in the cells and thus the protein can be produced. Initiation codons and stop codons are generally considered to be part of a nucleotide sequence that encodes the protein. However, it is preferred that these elements are functional in the cells. Similarly, promoters and polyadenylation signals used must be functional within the cells of the present invention. Examples of promoters useful to practice the present invention include but are not limited to promoters that are active in many cells such as the cytomegalovirus promoter, SV40 promoters and retroviral promoters. Other examples of promoters useful to practice the present invention include but are not limited to tissue-specific promoters, i.e. promoters that function in some tissues but not in others; also, promoters of genes normally expressed in the cells with or without specific or general enhancer sequences. In some embodiments, promoters are used which constitutively express genes in the cells with or without enhancer sequences. Enhancer sequences are provided in such embodiments when appropriate or desirable.

The cells of the present invention can be transfected using well known techniques readily available to those having ordinary skill in the art. Exogenous genes may be introduced into the cells using standard methods where the cell expresses the protein encoded by the gene. In some embodiments, cells are transfected by calcium phosphate precipitation transfection, DEAE dextran transfection, electroporation, microinjection, liposome-mediated transfer, chemical-mediated transfer, ligand mediated transfer or recombinant viral vector transfer.

In some embodiments, recombinant viral vectors are used to introduce DNA with desired sequences into the cell. In some embodiments, recombinant retrovirus vectors are used to introduce DNA with desired sequences into the cells. In some embodiments, standard calcium phosphate, DEAE dextran or lipid carrier mediated transfection techniques are employed to incorporate desired DNA into dividing cells. Standard antibiotic resistance selection techniques can be used to identify and select transfected cells. In some embodiments, DNA is introduced directly into cells by microinjection. Similarly, well-known electroporation or particle bombardment techniques can be used to introduce foreign DNA into the cells. A second gene is usually co-transfected or linked to the therapeutic gene. The second gene is frequently a selectable antibiotic-resistance gene. Transfected cells can be selected by growing the cells in an antibiotic that will kill cells that do not take up the selectable gene. In most cases where the two genes are unlinked and co-transfected, the cells that survive the antibiotic treatment have both genes in them and express both of them.

Methods and Uses of HSCs

Isolated HSCs are useful in a variety of ways. These cells can be used to reconstitute cells in a mammal whose cells have been lost through disease or injury. Genetic diseases may be treated by genetic modification of autologous or allogeneic HSCs to correct a genetic defect or to protect against disease. Diseases related to the lack of a particular secreted product such as a hormone, an enzyme, a growth factor, or the like may also be treated using HSCs. HSCs isolated and cultured as described herein can be used as a source of progenitor cells and committed cells to treat selected diseases as would be understood by those skilled in the art, including such diseases and/or injuries where the replacement of tissue by the cells of the present invention can result in a treatment or alleviation of the disease and/or injuries. HSCs cultured or expanded as described herein can be used, as cultured, or they can be used following differentiation into selected cell types, to treat a variety of disorders known in the art to be treatable using HSCs. The HSCs that are useful in these treatment methods include those that have, and those that do not have, an exogenous gene inserted therein.

The present invention encompasses methods for administering the cells of the present invention to an animal, including humans, in order to treat diseases where the introduction of new, undamaged cells will provide some form of therapeutic relief.

The cells of the present invention can be administered as HSCs or HSCs that have been induced to differentiate to exhibit at least one characteristic of the targeted cell type. The skilled artisan will readily understand that HSCs can be administered to a recipient as an undifferentiated cell and upon receiving signals and cues from the surrounding milieu, can differentiate into a desired cell type dictated by the neighboring cellular milieu. Additionally, HSCs can be administered as a purified population of cells, or as a heterogeneous mixture of cells, that contains HSCs as the active agent or cell type.

The cells can be prepared for grafting to ensure long term survival in the in vivo environment. For example, cells are propagated in a suitable culture medium for growth and maintenance of the cells and are allowed to grow to confluency. Any osmotically balanced solution which is physiologically compatible with the host subject may be used to suspend and inject the donor cells into the host. Formulations of a pharmaceutical composition suitable for parenteral administration comprise the active ingredient, i.e. the cells, combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents.

The invention also encompasses grafting HSCs (or differentiated HSCs) in combination with other therapeutic procedures to treat a disease or trauma. Thus, the cells of the invention may be co-grafted with other cells, both genetically modified or non-genetically modified cells which exert beneficial effects on the patient. Therefore the methods disclosed herein can be combined with other therapeutic procedures as would be understood by one skilled in the art once armed with the teachings provided herein.

The mode of administration of the cells of the invention may vary depending on several factors including the type of disease being treated, the age of the mammal, whether the cells are differentiated or not, whether the cells have heterologous DNA introduced therein, and the like. Cells may be introduced to the desired site by direct injection, or by any other means used in the art for the introduction of compounds. The cells can be administered into a host in a wide variety of ways. Modes of administration include, but are not limited to, intravascular, intracerebral, parenteral, intraperitoneal, intravenous, epidural, intraspinal, intrasternal, intra-articular, intra-synovial, intrathecal, intra-arterial, intracardiac, or intramuscular.

Transplantation of the cells of the present invention can be accomplished using techniques well known in the art as well as those described herein or as developed in the future. The present invention comprises a method for transplanting, grafting, infusing, or otherwise introducing HSCs into a mammal, preferably, a human.

In order to transplant the cells of the present invention into a human, the cells are prepared as described herein. Preferably, the cells are from the patient for which the cells are being transplanted into (autologous transplantation).

As contemplated herein, the present invention further provides for methods for use in various therapeutic interventions. For example, the methods of the present invention may be used in the treatment of bone marrow transplant donors and for recipients clinically by providing to either donors or recipients FDA approved medications that inhibit GSK-3 (such as lithium salts or other compounds that contain lithium) and mTOR (such as rapamycin) to expand HSCs and accelerate recovery from bone marrow suppression. In another example, the present invention provides a method for expansion of HSCs in culture using GS K-3 inhibitors and mTOR inhibitors. As demonstrated herein, inhibition of GSK-3 will activate downstream Wnt signaling in HSCs and will promote expansion of HSCs. As demonstrated herein, this can be a complex using FDA approved medications, such as lithium salts, which are already widely used clinically and are relatively safe. Applications apply to stem cells and other tissues, for example the skin and hair follicles (regeneration of skin and hair, burns, etc.), colon (regeneration of colonic epithelium, for example, after chemotherapy), and central nervous system (neuronal regeneration for neurodegenerative disorders). Further, the present invention may provide for ex vivo expansion of HSCs and improve transplantation, such as bone marrow transplantation, by expanding either short-term or long-term HSC's, or both, and improving initial survival, such as during the marrow suppression/peripheral cytopenia phase of BMT. Furthermore, these interventions make it possible to expand HSC's in human cord blood to improve the success of cord blood transplants. This approach can be more generally applicable to the ex vivo culture of human stem cells from somatic tissues, human embryonic stem cells, and induced pluripotent stem cells.

In one embodiment of the present invention, the method includes harvesting and culturing a patient's HSCs in culture medium containing at least one GSK-3 inhibitor and at least one mTOR inhibitor for treatment of cancers of the blood, such as leukemia and lymphoma, where the patient's cancerous hematopoietic cells were destroyed via radiation or chemotherapy and stem cells are replaced by stem cell transplantation (SCT). The method includes replacing the cultured HSCs via a bone marrow transplant. As used herein, the term "stem cell transplant" encompasses all forms of HSC transplant, including bone marrow, peripheral blood, and cord blood HSCs. In another embodiment, the method includes the transplanting of HSCs collected from the peripheral circulation of a matched donor. In another embodiment, the method includes the transplanting of HSCs collected from human umbilical cord blood (hUCB). As contemplated herein, and without limitation, the cultured HSCs may be used to treat cancers of the blood such as acute lymphoblastic leukemia, acute myeloblastic leukemia, chronic myelogenous leukemia (CML), Hodgkin's disease, multiple myeloma, and non-Hodgkin's lymphoma and neoplastic diseases of the blood including myelodysplasia and myeloproliferative disease.

In another embodiment, the aforementioned methods may be used in the treatment of bone marrow failure syndromes including aplastic anemia, whether acquired or inherited, and paroxysmal nocturnal hemoglobinuria.

In another embodiment, the aforementioned methods may be used in the treatment of hereditary blood disorders, such as different types of inherited anemia (failure to produce blood cells), and inborn errors of metabolism (genetic disorders characterized by defects in key enzymes need to produce essential body components or degrade chemical byproducts). Without limitation, such blood disorders treatable by the methods of the present invention may include aplastic anemia, beta-thalassemia, Blackfan-Diamond syndrome, globoid cell leukodystrophy, sickle-cell anemia, severe combined immunodeficiency, X-linked lymphoproliferative syndrome, and Wiskott-Aldrich syndrome. Without limitation, inborn errors of metabolism that are treatable with the methods of the present invention include Hunter's syndrome, Hurler's syndrome, Lesch Nyhan syndrome, and osteopetrosis. Because bone marrow transplantation has carried a significant risk of death, this is usually a treatment of last resort for otherwise fatal diseases.

As chemotherapeutic techniques aimed at rapidly dividing cancer cells inevitably hit rapidly dividing hematopoietic cells, the methods of the present invention may also be used in treating cancer patients with an autologous stem cell transplant to replace the cells destroyed by chemotherapy. The method may include mobilizing HSCs, collecting them from peripheral blood, and culturing the cells in culturing medium containing at least one GSK-3 inhibitor and at least one mTOR inhibitor. The cells may then be stored, such as via cryopreservation, while the patient undergoes intensive chemotherapy or radiotherapy to destroy the cancer cells. Once the chemotherapy or radiotherapy is completed, the patient may receive a transfusion of his or her stored HSCs.

In yet another embodiment, the methods of the present invention may be used for treating otherwise untreatable tumors, such as for the treatment of metastatic kidney cancer or solid tumors that resist standard therapy, including cancer of the lung, prostate, ovary, colon, esophagus, liver, and pancreas. For example, the method may include an allogeneic stem cell transplant from an HLA-matched sibling whose HSCs are collected peripherally and cultured in a culturing medium containing at least one GSK-3 inhibitor and at least one mTOR inhibitor. The method includes transfusing the donor's cultured HSCs into the patient, followed by monitoring the patient's immune cells, such as via DNA fingerprinting, to follow the engraftment of the donor's cells and regrowth of the patient's own blood cells.

In other embodiments, the aforementioned methods may be used for treating other diseases, such as diabetes, rheumatoid arthritis, system lupus erythematosis and other autoimmune diseases. For example, HSCs cultured in the presence of at least one GSK-3 inhibitor and at least one mTOR inhibitor may be genetically modified for delivery of genes to repair damaged cells. As contemplated herein, the methods of the present invention may be used for treating any disease, disorder or condition in which HSCs are used.

Kits

The present invention further includes various kits which comprise a culturing medium, including at least one GSK-3 inhibitor and at least one mTOR inhibitor, and instructional materials which describe use of the culturing medium to perform the methods of the invention. Although model kits are described below, the contents of other useful kits will be apparent to the skilled artisan in light of the present disclosure. Each of these kits is contemplated within the present invention.

In one aspect, the invention includes a kit for maintaining and expanding HSCs ex vivo. The kit is used in the same manner as the methods disclosed herein for the present invention. Briefly, the kit may be used to maintain and expand freshly harvested HSCs or cryopreserved HSCs in culture. The kit may further include cryopreserved HSCs. The cryopreserved HSCs may be provided in an appropriate amount as set forth elsewhere herein. The kit may further include genetically modified HSCs. The kit may further include at least one cytokine or a promotion factor. Additionally, the kit comprises instructional material for the use of the kit. These instructions simply embody any of the examples and embodiments provided herein.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXAMPLES

The invention is now described with reference to the following Examples. These Examples are provided for the purpose of illustration only, and the invention is not limited to these Examples, but rather encompasses all variations which are evident as a result of the teachings provided herein.

The materials and methods employed in the experiments and examples disclosed herein are now described.

Mice: C57BL/6 WT (CD45.2), CD45.1 congenic (The Jackson Laboratory), and Mx-cre; β-catenin$^{fl/fl}$ mice were bred in house in a pathogen-free mouse facility of the University of Pennsylvania. Transplant recipients were female mice 10-12 weeks old. All work with mice was done according to a protocol reviewed and approved by the Institutional Animal Care and Use Committee at the University of Pennsylvania.

FCM and HSC isolation: BM cells were flushed from the long bones (tibias and femurs) of mice with Hank's buffered salt solution without calcium or magnesium, supplemented with 2% heat-inactivated calf serum. For detection of LSK Flk2 CD34 cells, whole BM cells were incubated with Biotin-conjugated monoclonal antibodies to lineage markers, including B220 (6B2), CD4 (GK1.5), CD8 (53-6.7), Gr-1 (8C5), Mac-1 (M1/70), Ter119, and IL-7R (A7R34), in addition to PE Cy5.5-conjugated anti-Sea-1 (Ly6A/E; D7), allophycocyanin-Alexa Fluor 750-conjugated anti-c-kit (ACK2), PE-conjugated anti-Flk2 (Ly-72/A2F10), and Alexa Fluor 647-conjugated anti-CD34. Biotin-conjugated lineage markers were detected using streptavidin-conjugated PE-Texas Red. Nonviable cells were excluded from sorting and analyses using the viability dye DAPI (1 g/ml). Cells were sorted with a FACSAria (BD) or MoFlo (Cytomation) automated cell sorter. Analysis was performed on LSR II or FACSCalibur flow cytometer (BD). Data were analyzed using FlowJo software (Tree Star).

Constructs and lentiviruses: shRNAs sequences were designed using software from the Broad Institute (http://www.broad.mit.edu/genome_bio/trc/publicSearchForHairpinsForm.php), which identified 5 potential shRNA sequences in Gsk-3 and PTEN. The shRNAs were cloned into the H1UG1 lentivirus (Balint, et al., 2005, J. Clin. Invest. 115:3166-3176), a 4-component, replication-incompetent system derived from FG12 (Qin, et al., 2003, Proc. Natl. Acad. Sci. U.S. A. 100:183-188), which uses the human UI promoter to drive shRNA expression and the human Ubiquitin-C promoter to drive expression of GFP for lineage tracing. H1UG1 was provided by A. Gewirtz (University of Pennsylvania School of Medicine). High-titer lentiviral supernatant was produced by transient transfection of 293T cells and was tested in NIH3T3 cells.

BM transduction and transplantation: Lentiviral transduction of 5-FU-treated BM cells and transplantation into lethally irradiated (10 Gy) recipients was performed as described previously (Pui, et al., 1999, Immunity. 11:299-308).

Cell cycle analysis and BrdU incorporation: Sorted GFP$^+$ LSK and GFP$^+$ LSK Flk2$^-$ cells from primary recipients of Gsk3-rnai or vector control for 4 months were incubated, as described previously (Bersenev, et al., 2008, J. Clin Invest. 118:2832-2844), with 5 μg/ml Hoechst 33342 (Invitrogen) in HBSS containing 20 mM HEPES, 5 mM glucose, and 10% FBS at 37° C. for 45 minutes, then incubated for 45 minutes with 1 μg/ml Pyronin (Sigma-Aldrich), and analyzed with an LSRII flow cytometer (BD Biosciences). For BrdU labeling, primary recipients of Gsk3-rnai or vector control were fed 0.5 mg/ml BrdU in the drinking water for the last 7 days of a 4-month transplant, and GFP$^+$ LSK Flk2$^+$ and GFP$^+$ LSK Flk2$^-$ cells were sorted. BrdU incorporation was determined by FACS analysis using APC-conjugated antibodies specific to BrdU and PI according to the manufacturer's protocol (BD Biosciences).

Long-term noncompetitive repopulation assay: Adult recipient mice were irradiated with a Cs-137 Irradiator in 2 equal doses of 5 Gy separated by at least 2 hours. Cells were injected into the retroorbital venous sinus of anesthetized recipients. Each secondary recipient mouse received $2 \times 10^5$ sorted GFP+BM cells from primary recipients of Gsk3-rnai or vector control, and each tertiary recipient mouse received $4 \times 10^5$ sorted GFP+BM cells from secondary recipients. Beginning 4 weeks after transplantation and continuing for at least 16 weeks, blood was collected from the tail veins of recipient mice, red blood cells were lysed by ammonium chloride-potassium (Ack) buffer, and the remaining cells were stained with directly conjugated antibodies to B220 (6B2), Mac-1 (M1/70), CD4 (L3T4), CD8 (Ly-3), and Gr-1 (8C5) to monitor engraftment by FCM.

Long-term competitive repopulation assay: Sorted GFP+ cells from primary recipients of Gsk3-rnai or vector control (tester) were transplanted into lethally irradiated B6 recipients together with $2 \times 10^5$ competitor B6 BM cells (CD45.2+; Bersenev, et al., 2008, J. Clin Invest. 118:2832-2844; Szilvassy, et al., 1990, Proc. Natl. Acad. Sci. U.S.A. 87:8736-8740; Maillard, et al., 2008, Cell Stem Cell. 2:356-366). In limiting dilution analyses, decreasing numbers of tester GFP+ cells were used (i.e., $1 \times 10^6$, $5 \times 10^5$, $1 \times 10^5$, and $2 \times 10^4$). Beginning 4 weeks after transplantation and up to 16 weeks, blood was collected from the tail veins of recipient mice, red blood cells were lysed in Ack buffer, and the remaining cells were stained with directly conjugated antibodies to B220 (6B2), Mac-1 (M1/70), CD4 (L3T4), CD8 (Ly-3), and Gr-1 (8C5) to monitor engraftment by FCM. Blood and BM were analyzed 16 weeks after transplantation. The number of competitive repopulation units was calculated with L-Calc software (StemCell Technologies; Bersenev, et al., 2008, J. Clin Invest. 118:2832-2844; Maillard et al., 2008, Cell Stem Cell. 2:356-366).

Methylcellulose culture: Sorted GFP+ BM cells were plated in individual wells of 6-well plates (Corning) containing 550 µl 1.0% methylcellulose (Stem Cell Technologies) as previously described (Trowbridge, et al., 2006, Nature. 441: 518-522). The methylcellulose was supplemented with 1% penicillin/streptomycin (Gibco; Invitrogen), 50 ng/ml SCF, 10 ng/ml IL-3, 10 ng/ml IL-6, and 3 U/ml erythropoietin. Colonies were incubated at 37° C. in humidified incubators at 5% $CO_2$. Colony formation was scored by counting all colonies of greater than 30 viable cells after 10-14 days of culture.

Administration of polyI:polyC and rapamycin: As described previously (Cobas, et al., 2004, J. Exp. Med. 199: 221-229), polyI:polyC (Sigma-Aldrich) was resuspended in Dulbecco PBS at 2 mg/ml. Mice received 25 µg/g polyI: polyC every other day for 2 weeks. Rapamycin (LC Laboratories) was dissolved in absolute ethanol at 10 mg/ml and diluted in 5% Tween-80 (Sigma-Aldrich) and 5% PEG-400 (Hampton Research) before injection and was administered by intraperitoneal injection at 4 mg/kg rapamycin in 200 µl total volume/injection every other day for 8 weeks.

Statistics: All data are mean±SD. Statistical significance was determined by a 2-tailed Student's t test, and a P value less than 0.05 was considered significant.

The results of the experiments presented herein are now described.

Example 1

Lithium Increases Hematopoietic Stem/Progenitor Cells

Lithium increases circulating CD34+ stem cells (Bailin, et al., 1998, Br J Haematol 100:219-221) in humans, increases neutrophil count in a high percentage of treated patients, and may also stimulate other lineages (Shopsin, et al., 1971, Clin Pharmacol Ther 12:923-928; Boggs, et al., 1983, Seminars in Hematology 20:129-138; Barr, et al., 1983, Canadian Medical Association Journal 128:123-126; Tisman, et al., 1972, British Journal of Haematology 24:767-771; Joyce, 1984, British Journal of Haematology 56:307-321; Bille, et al., 1975, Acta Medica Scandinavica 198:281-286; Ricci, et al., 1981, Haematologica 66:627-633; Focosi, et al., 2009, Journal of Leukocyte Biology 85:20-28). In rodents, lithium increases peripheral blood counts and enhances stem and progenitor cell numbers in ex vivo and in vivo assays. These studies led to the hypothesis that the effects of lithium are mediated at the level of the HSC and/or HPC (Joyce, 1984, British Journal of Haematology 56:307-321; Gallicchio et al., 1992, Journal of Medicine 23:195-216; Gallicchio, et al., 1980, Blood 56:1150-1152). With immunophenotypic markers to detect diverse hematopoietic cell types, the effect of lithium has been reexamined on hematopoiesis in C57/B6 mice using FCM.

Mice received dietary LiCl (or NaCl as control) at a dose that achieves a serum lithium concentration of 1.0 mEq/L (O'Brien, et al., 2004, Journal of Neuroscience 24:6791-6798), similar to therapeutic concentrations in bipolar disorder patients (there was no change in the overall well being of the animals after two-three weeks on lithium). After 2 weeks, bone marrow was isolated and cells were analyzed by FCM. Lithium caused a significant increase in the number of LSK cells compared with NaCl treated animals, as depicted in FIG. 1A, consistent with an increase in HSCs and HPCs, and a doubling of the overall marrow cellularity, as depicted in FIG. 1B. To confirm this, the expression of the SLAM family receptors CD150, CD48, and CD244 was examined (Kiel, et al., 2005, Cell 121:1109-1121) and it was observed that there was an approximately 2.3-fold increase in the number of CD150+CD48−CD244− cells, an immunophenotypic population highly enriched for HSCs (data not shown). Histological analysis of bone marrow morphology showed no significant differences in maturity or cellular morphology in lithium-treated versus control marrows, as reported previously (not shown). Consistent with published observations in humans and rodents, the percentage of neutrophils in peripheral blood also increased 30-40% in lithium-treated mice (data not shown). Inclusion of CD34 and Flk2 in FCM analysis shows that lithium primarily increases the CD34+Flk2− population, consistent with an increase in ST-HSCs, also depicted in FIG. 1A.

Example 2

GSK-3 as the Target of Lithium in HSC/HPCs

Inhibition of GSK-3 provides a compelling explanation for many of the known effects of lithium (Klein, et al., 1996, Proc. Nat'l. Acad. Sci. U.S.A. 93:8455-8459), but lithium also inhibits inositol monophosphatase and structurally related phosphomonoesterases, some of which are highly sensitive to lithium (Gurvich et al., 2002, Pharmacol Ther 96:45-66). To test further whether inhibition of GSK-3 explains the hematopoietic effects of lithium, selective GSK-3 inhibitors were used that are unlikely to have off-target effects that overlap with lithium (Bain, et al., 2003, Biochem J 371 (Pt. 0:199-204; Meijer, et al., 2003, Chem Biol 10:1255-1266; Williams, et al., 2005, Angew Chem Int Ed Engl. 44:1984-1987). The selective GSK-3 inhibitor, 6-bromo-indirubin 3'-oxime (6BIO) has an 1050 for GSK-3 in the nanomolar range (Meijer, et al., 2003, Chem Biol 10:1255-1266). 6BIO caused a pronounced increase in the number of LSK cells after a 2-week treatment, as depicted in FIG. 1C. 6BIO also increased marrow cellularity, similar to lithium. These observations are consistent with Trowbridge et al, who observed an approximately 50% increase in LSK cells in mice treated with the GSK-3 inhibitor CHIR-911 (Trowbridge, et al., 2006, Nat Med 12:89-98). Goessling et al also reported that 6BIO increases HSCs in mice as measured by long-term competitive repopulation assay (Goessling, et al., 2009, Cell 136:1136-1147), consistent with the observation of increased LSK cells after 6B10 treatment described herein. Taken together, these pharmacological data support the hypothesis that lithium increases HSCs through inhibition of GSK-3.

To test whether progenitor cells are increased by lithium treatment, colony formation assays were performed. Previous work in the 1980's with lithium-treated rodents demonstrated an increase in colony forming units (CFU) in ex vivo assays and by CFU-S formation in short-term transplants (Joyce, 1984, British Journal of Haematology 56:307-321; Levitt, et al., 1980, New England Journal of Medicine 302:713-719). To confirm these studies, bone marrow cells were isolated from lithium treated mice and cultured in methylcellulose with hematopoietic cytokines. Marrow from lithium treated animals showed a two-fold increase in total colony initiating cells compared to control, similar to earlier reports (data not shown) and consistent with more recent observations with small molecule GSK-3 inhibitors, which increase CFUs ex vivo and CPU-S approximately 1.5 to 2-fold (Trowbridge, et al., 2006, Nat Med 12:89-98; Goessling, et al., 2009, Cell 136:1136-1147).

To test in a side-by-side comparison whether structurally diverse GSK-3 inhibitors expand HPCs similar to lithium, c-Kit+ cells were purified from control mice and treated for three days with GSK-3 inhibitors including lithium, 6BIO (Meijer, et al., 2003, Chem Biol 10:1255-1266; Goessling, et al., 2009, Cell 136:1136-1147), AR-A014418 (Bhat, et al., 2003, Journal of Biological Chemistry 278:45937-45945), and the organometallic GSK-3 inhibitor DW21 (Williams, et al., 2005, Angew Chem Int Ed Engl. 44:1984-1987). The number of cells after three days was similar in each group, as depicted in FIG. 1E, Treated cells were washed and an equal number from each sample was then added to methylcellulose with hematopoietic cytokines and cultured for 10-14 days. Each of the GSK-3 inhibitors induced a marked increase in hematopoietic colony number, as depicted in FIG. 1D, strongly supporting the hypothesis that lithium expands the HPC population by inhibiting GSK-3 within hematopoietic cells.

Example 3

Gsk-3 Loss of Function in Hematopoietic Cells

Therapeutic lithium increases the number of circulating $CD34^+$ stem cells in humans (Ballin, et al., 1998, Br. J. Haematol. 100:219-221), increases peripheral blood counts, especially neutrophils, in a high percentage of treated patients, and enhances stem and progenitor cell numbers in rodents (Boggs, et al., 1983, Semin. Hematol. 20:129-138; Joyce, 1984, Br. J. Haematol. 56:307-321; Ricci, et al., 1981, Haematologica. 66:627-633; Focosi, et al., 2009, J. Leukoc. Biol. 85:20-28; Gallicchio, et al., 1992, J. Med. 23:195-216; Gallicchio, et al., 1980, Blood. 56:1150-1152). However, since these early studies were performed, immunophenotypic markers of HSCs and HPCs have become available (Purton, et al., 2007, Cell Stem Cell. 1:263-270). Flow cytometry (FCM) on BM from lithium-treated mice were used, and an increase in immunophenotypic HSCs/HPCs was found, as detected by LSK markers (Purton, et al., 2007, Cell Stem Cell. 1:263-270; See FIG. 1A) or by detection of the SLAM marker immunophenotype ($CD150^+CD48^-$) characteristic of HSCs (Kiel, et al., 2005, Cell. 121:1109-1121; data not shown). The selective GSK-3 inhibitor 6-bromo-indirubin 3'-oxime (6BIO) also increased the number of LSK cells after 2 weeks, as depicted in FIG. 1C, consistent with recent reports using 6BIO (Goessling, et al., 2009, Cell. 136:1136-1147) or the GSK-3 inhibitor CHIR-911 (Trowbridge, et al., 2006, Nat. Med, 12:89-98). It was also observed herein that a parallel increase in BM cellularity after treatment with either lithium or 6BIO, with no observable change in BM architecture, as depicted in FIG. 1B (also data not shown). Lithium, 6BIO, AR-A014418, and other structurally distinct GSK-3 inhibitors also increased hematopoietic colony formation ex vivo, as depicted in FIG. 1D.

Figures 2A, 2B, 2C, 2D:
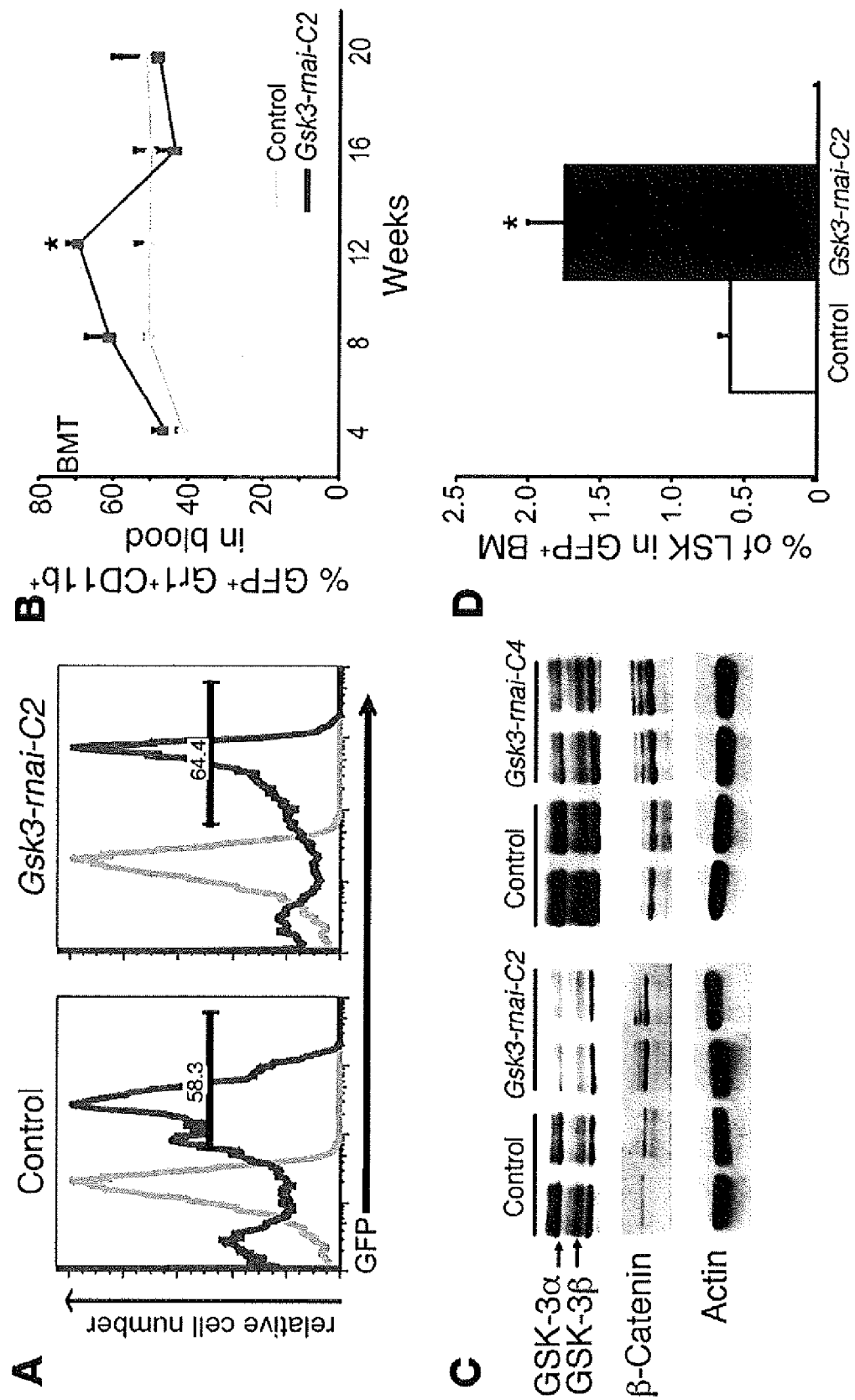
FIG. 2B depicts GFP$^+$ myeloid cells (Gr1$^+$CD11b$^+$) in peripheral blood for 10 control and 9 Gsk3-rnai-C2 recipients after BM transplantation (BMT; arrow). Depicted in FIG. 2C are immunoblots for GSK-3alpha/beta and beta-catenin in BM from primary recipients 16 weeks after transplantation. Data represent independent replicates from 6 control and 6 Gsk3-rnai recipients.
FIG. 2D depicts the percent GFP$^+$ LSK cells in control and Gsk3-rnai-C2 primary recipients.

The parallel effects of lithium and alternative GSK-3 inhibitors support the hypothesis that GSK-3 is a significant target of lithium in HSCs/HPCs and suggest a critical function for GSK-3 in hematopoiesis. However, results based on systemically delivered inhibitors do not address whether GSK-3 functions cell autonomously in HSCs/HPCs; in addition, off-target effects remain a formal possibility. As Gsk-3 loss of function has not previously been reported in HSCs, depletion of Gsk-3 in BM cells was tested using RNAi and conventional Gsk3b KO (Hoeflich, et al., 2000, Nature. 406: 86-90). Two distinct shRNAs that target sequences conserved in both Gsk3a and Gsk3b were cloned into a lentivirus that also expresses GFP (Balint, et al., 2005, J. Clin. Invest. 115: 3166-3176). Donor BM cells were infected with control or shRNA constructs (Gsk3-rnai-C2 and Gsk3-rnai-C4) and transplanted into lethally irradiated primary recipients. Peripheral blood was sampled at 4-week intervals for 20 weeks to confirm engraftment. After 8 weeks, a majority of peripheral blood cells in both Gsk3-rnai and control vector transplants were derived from $GFP^+$ donor cells, including T cells ($CD4^+$ and $CD8^+$), B cells ($B220^+$), myeloid cells ($Gr1^+$ $CD11b^+$), and erythroid cells ($TER119^+$), indicating successful engraftment and reconstitution, as depicted in FIG. 2A (other data not shown). The contribution to the mature myeloid lineage, as marked by $Gr1^+CD11b^+$ cells, was increased at 8 and 12 weeks in hosts receiving Gsk3-rnai BM, as depicted in FIG. 2B, similar to known effects of lithium treatment (Boggs et al., 1983, Semin. Hematol. 20:129-138; Joyce, 1984, Br. J. Haematol. 56:307-321; Ricci, et al., 1981, Haematologica. 66:627-633; Focosi, et al., 2009, J. Leukoc. Biol. 85:20-28; Gallicchio, et al., 1992, J. Med. 23:195-216; Gallicchio, et al., 1980, Blood. 56:1150-1152). GSK-3α and GSK-3β protein levels remained low in BM harvested from primary recipients 4 months after transplantation with both Gsk3-rnai vectors, but not with control lentivirus, as depicted in FIG. 2C. Furthermore, β-catenin protein levels were elevated in Gsk3-depleted BM cells harvested from primary recipients of Gsk3-rnai cells, also depicted in FIG. 2C, consistent with reduced GSK-3-dependent phosphorylation and activation of Wnt signaling. Because subsequent results with the Gsk3-rnai-C2 and Gsk3-rnai-C4 constructs were similar, only data using the Gsk3-rnai-C2 construct are shown.

Figures 2E, 2F, 2G, 2H:
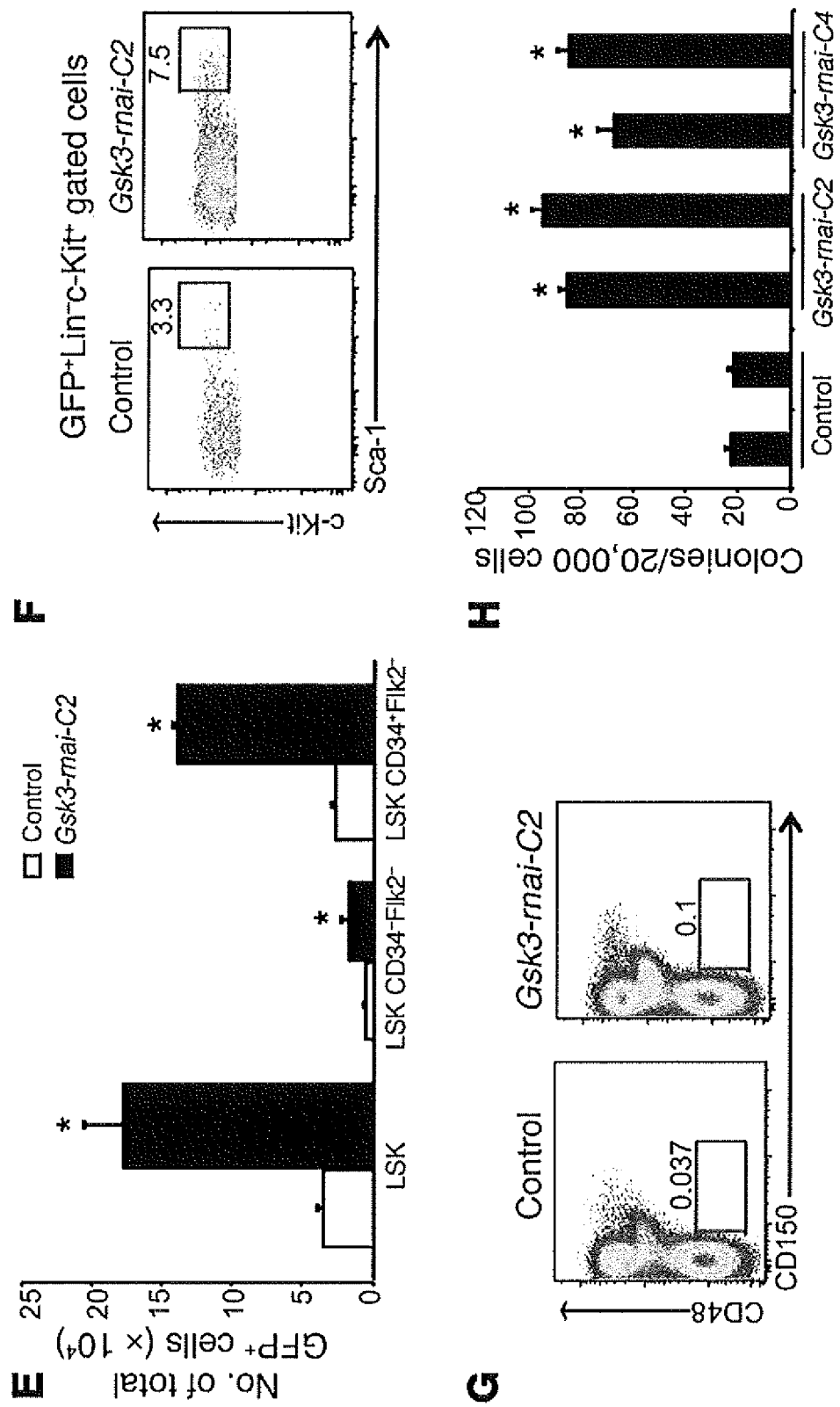
FIG. 2E depicts absolute number of GFP$^+$ LSK, LSK CD34$^-$Flk2$^-$, and LSK CD34$^+$Flk2$^-$ cells.
FIG. 2F depicts representative FCM showing GFP$^+$ cells in the HSC-containing LSK fraction (red gate) for control and Gsk3-rnai-C2 primary recipients.
FIG. 2G depicts representative FCM using SLAM markers, where the difference between control and Gsk3-rnai was significant (P<0.05). The numbers in FIGS. 2F and 2G indicate percent cells within gates.
FIG. 2H depicts colony formation using GFP$^+$ cells plated in methylcellulose with cytokines and scored for CFU-C. Data represent mean colonies per well performed in duplicate groups for 5 mice per construct repeated in 3 separate experiments. *P<0.05 versus respective control value.
Figures 3A, 3B:
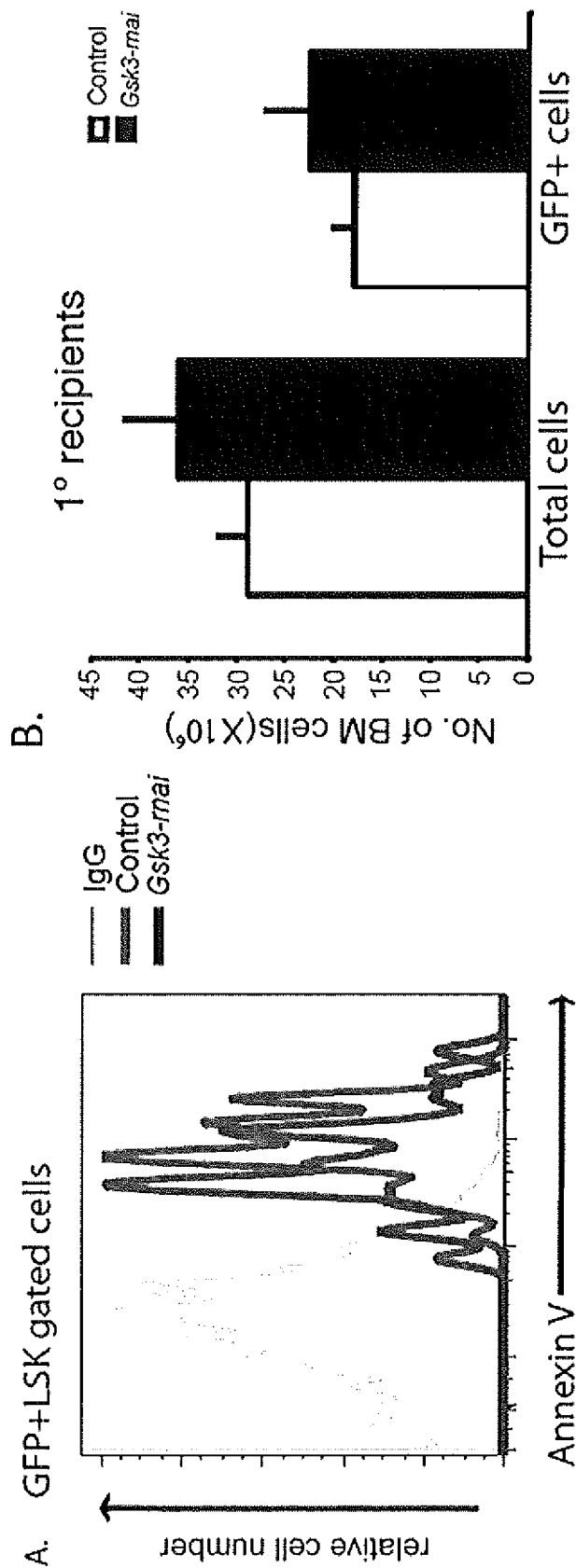
FIGS. 3A-D, depicts annexin V staining and cellularity of bone marrow harvested from transplant recipients.
Figures 3C, 3D:
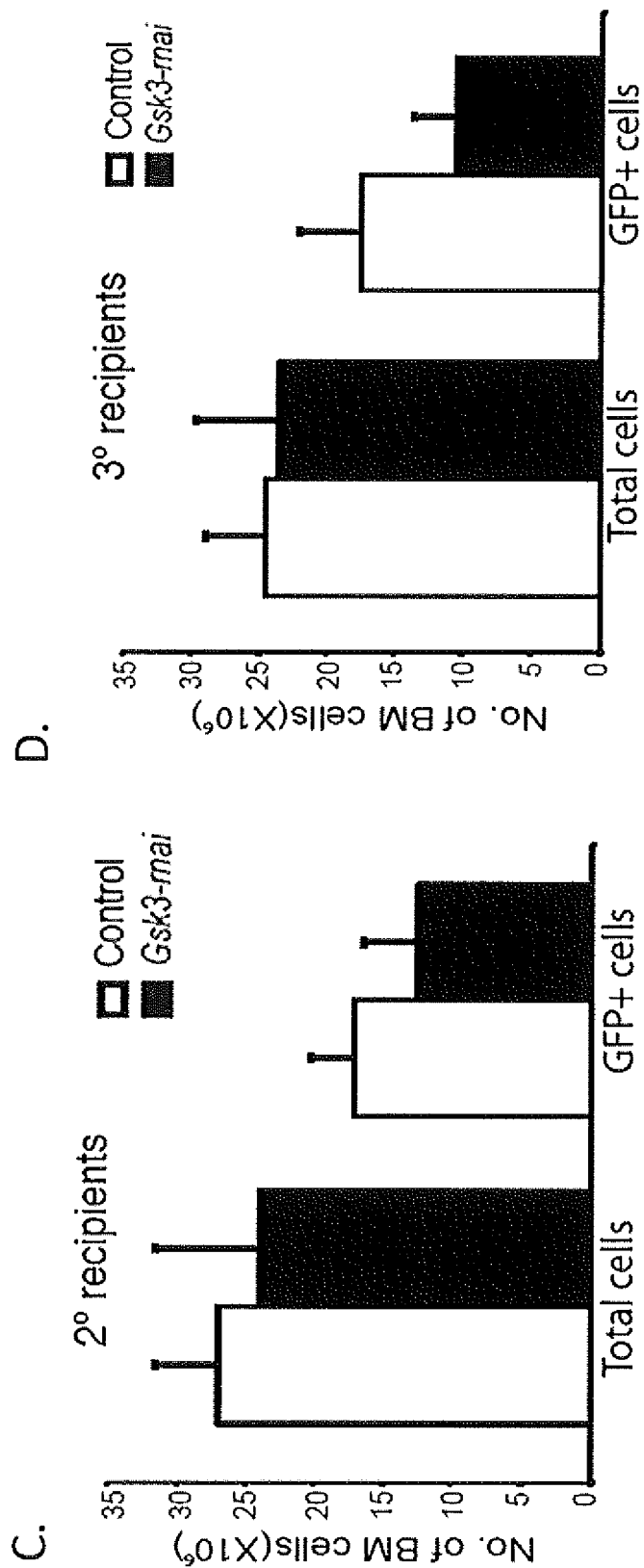

Importantly, both percentage and number of immunophenotypic HSCs/HPCs increased greater than 4-fold in Gsk3-rnai-transduced cells compared with control cells, as assessed by the increase in $GFP^+$ LSK cells and depicted in FIGS. 2D-2F, as well as $CD150^+CD48^-$ cells, as depicted in FIG. 2G. Multiparametric FCM analysis of CD34 and flk-2 showed an increase in immunophenotypic short-term HSCs (ST-HSCs) and long-term HSCs (LT-HSCs; FIG. 2E). The total cellularity of the BM was only marginally increased, as depicted in FIG. 3B, in contrast to the effect of the systemically delivered GSK-3 inhibitors (FIG. 1B). Furthermore, BM harvested at 4 months from primary transplants of Gsk3-rnai-transduced BM yielded greater than 4-fold more colonies in methylcellulose culture than did control BM, as depicted in FIG. 2H.

Figure 4A:
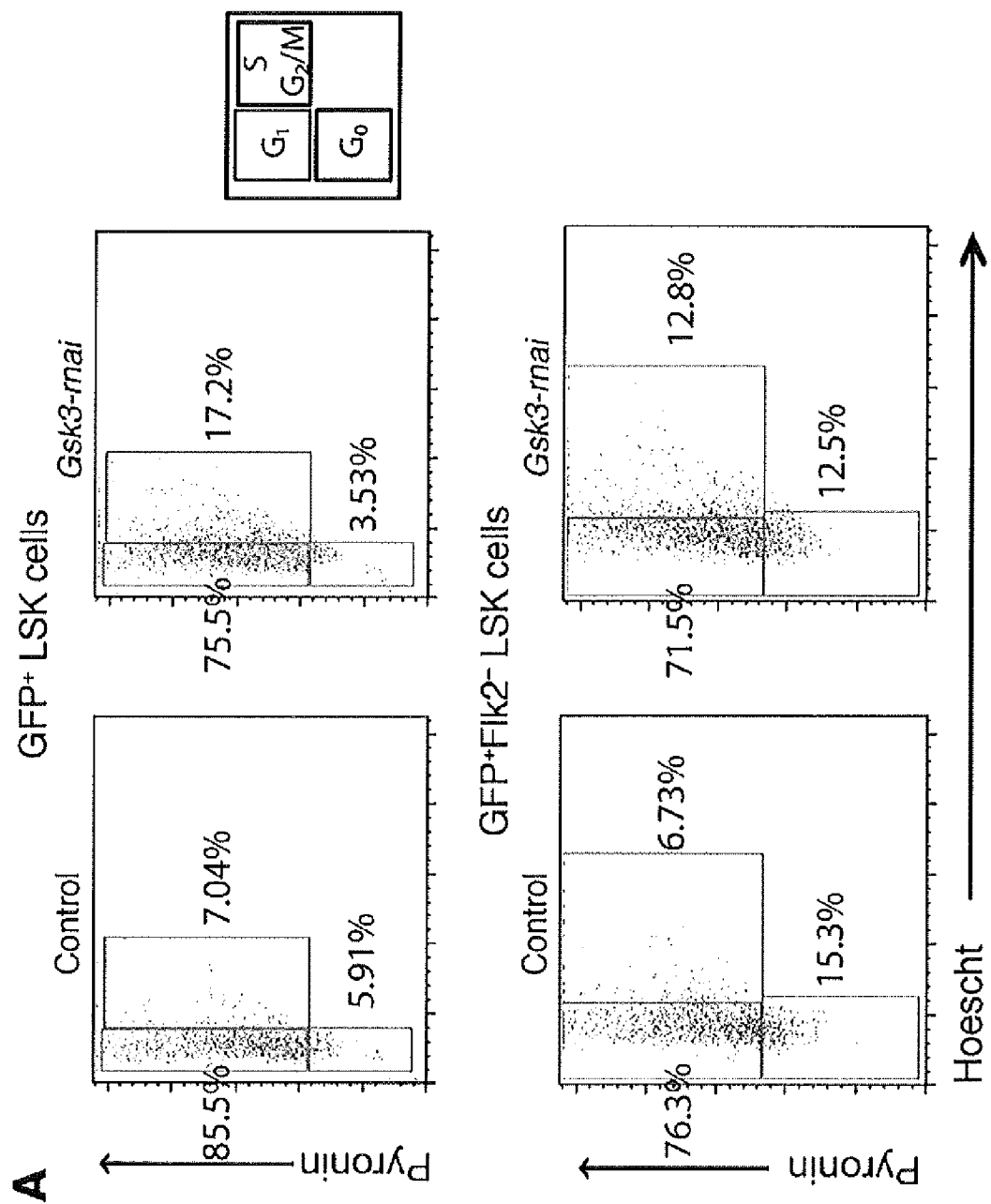
In FIGS. 4A and 4B, lower left gate represents G$_0$, upper left represents G$_1$, and upper right represents S, G$_2$, and M phases of the cell cycle, as shown in the diagram in FIG. 4A.
Figure 4B:
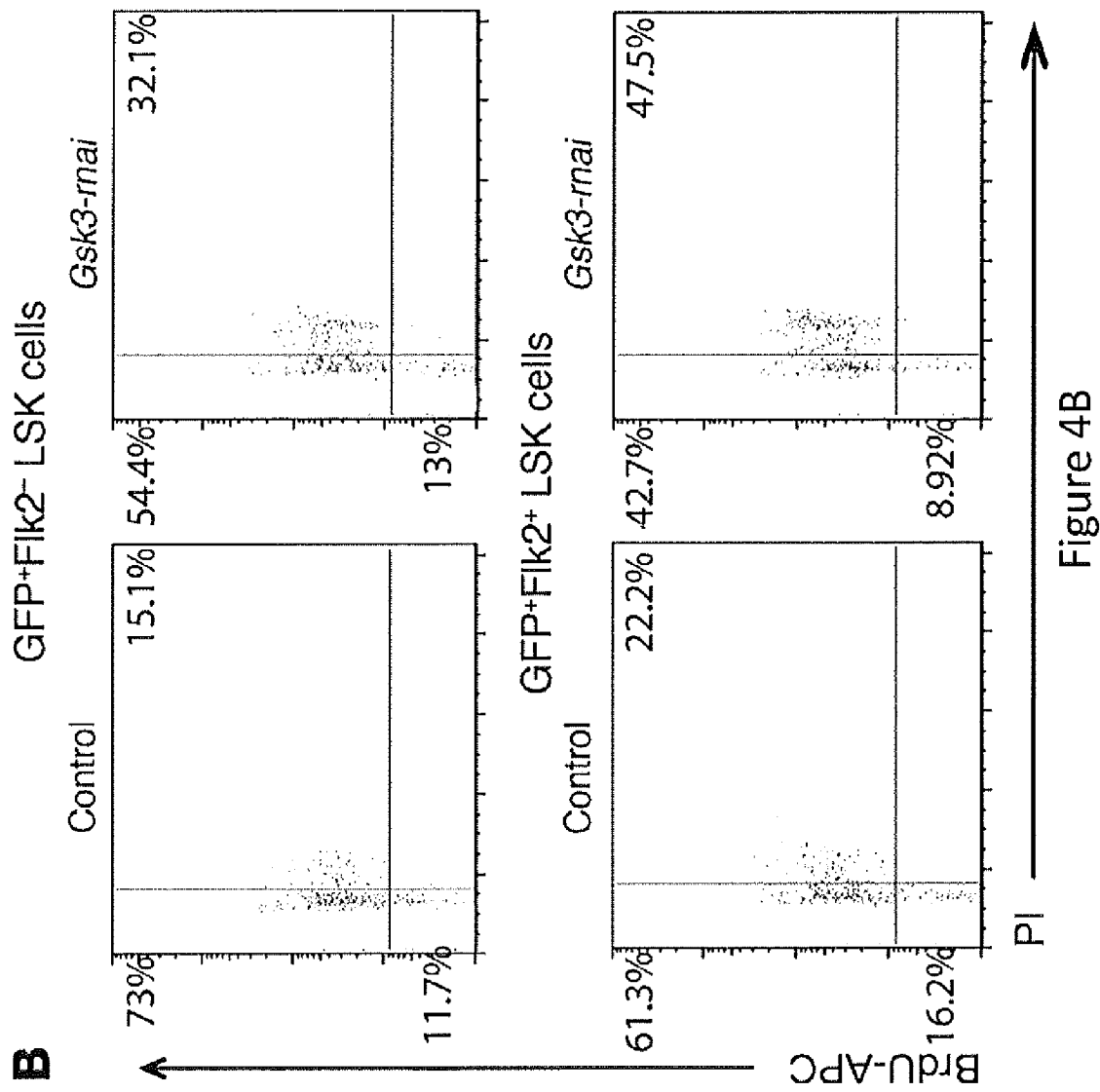

To explore the mechanism by which Gsk-3 depletion expands the size of the phenotypic HSC/HPC pool, the cell cycle and survival status of GFP-marked LSK cells was examined. $GFP^+$ LSK or $GFP^+$ LSK $Flk2^-$ cells were purified from control or Gsk3-rnai-transduced BM after 4-5 months in primary recipients and stained with pyronin and Hoechst followed by FCM (Bersenev, et al., 2008, J. Clin Invest. 118:2832-2844). Compared with controls, approximately 2-fold more Gsk3-depleted cells had entered the $S/M/G_2$ phases of the cell cycle in both the $GFP^+$ LSK and $GFP^+$ LSK $Flk2^-$ populations, as depicted in FIG. 4A, demonstrating increased cycling of Gsk3-deficient LSK cells. Transplant recipients were also fed BrdU for 7 days prior to BM harvest. Incorporation of BrdU coupled with analysis of propidium iodide (PI) staining confirmed that Gsk-3 depletion increased the percentage of LSK cells in $S/M/G_2$ more than 2-fold, as depicted in FIG. 4B. Annexin V staining in Gsk3-deficient LSK cells was not significantly different from that of controls (FIG. 3A), indicating that the increase in LSK cells is not caused by a change in the rate of cell death. These data indicate that loss of Gsk-3 results in accelerated cell cycle progression within the LSK cell population.

Example 4

Functional HSCs are Reduced in Gsk3-Deficient BM

Figure 5:
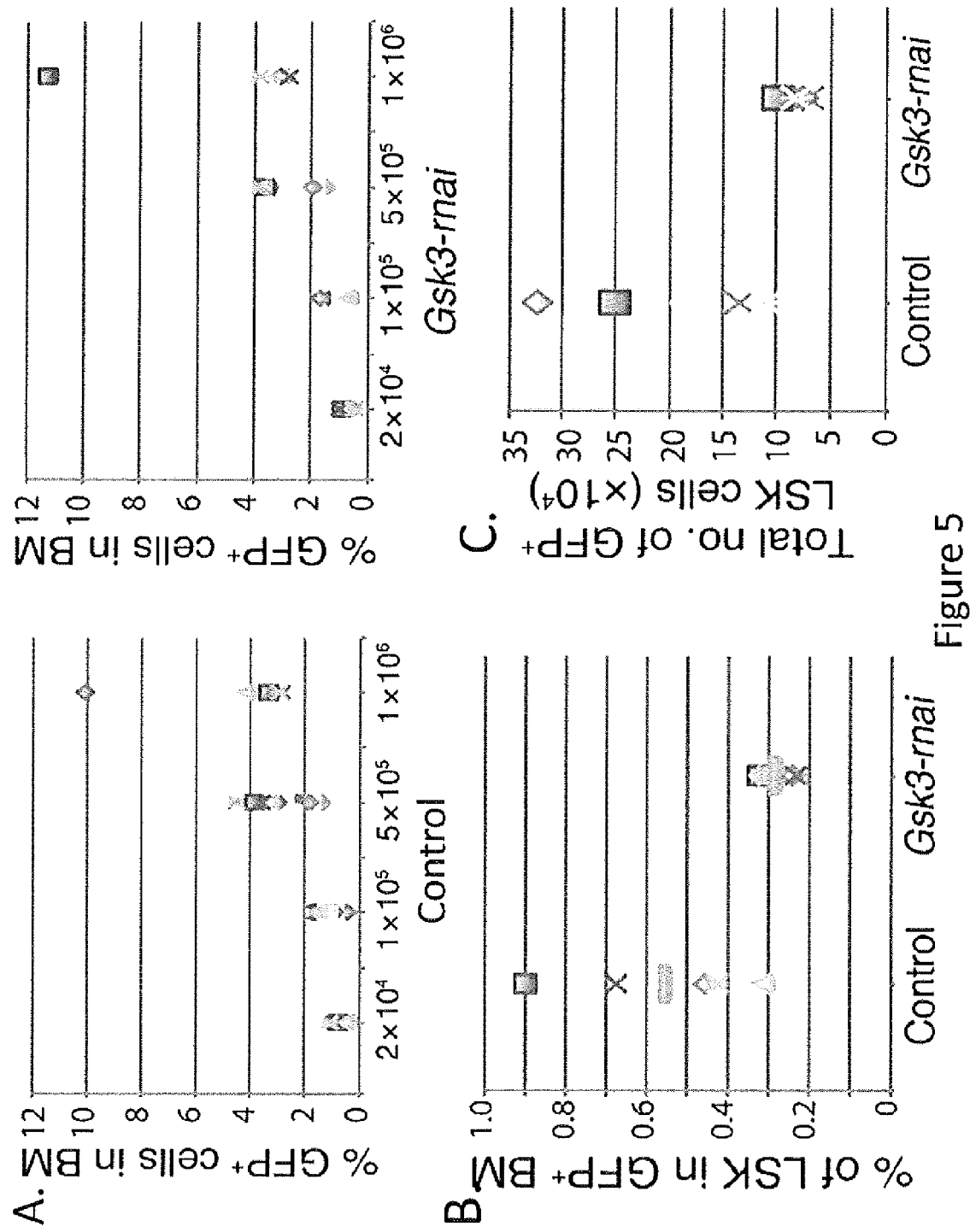
FIG. 5, comprising FIGS. 5A-C, demonstrates that Gsk3-depleted HSCs are functionally deficient. As depicted in FIG. 5A, limiting dilution experiments were performed with 4 doses (x axis) of GFP$^+$ test BM from vector-control and Gsk3-rnai primary recipients (4 donors per group) combined with a fixed number (2×10$^5$) unlabeled competing cells transplanted into groups of at least 5 recipients per dose. Chimerism at 4 months after transplantation for each dose is represented as the percentage of GFP$^+$ cells in BM for control and Gsk3-rnai. Depicted in FIG. 5B are percent donor-derived immunophenotypic HSCs/HPCs (as GFP$^+$ LSK cells) in the 1×10$^6$ test cell group 4 months after transplantation. Depicted in FIG. 5C are absolute number of donor-derived immunophenotypic HSCs/HPCs (as GFP$^+$ LSK cells) in the 1×10$^6$ test cell group 4 months after transplantation.

Because inhibition of GSK-3 activity or expression increased immunophenotypic HSCs and HPCs and increased functional HPCs within the LSK cell population, competitive repopulating units were measured (Szilvassy, et al., 1990, Proc. Natl. Acad. Sci. U.S.A. 87:8736-8740) as a functional test of HSCs in Gsk3-depleted versus control BM. Control and Gsk3-rnai-infected BM was transplanted to irradiated recipients and harvested after 4 months. Sorted $GFP^+$ cells were mixed at dilutions from $2 \times 10^4$ to $1 \times 10^6$ cells with a constant number ($2 \times 10^5$) of $GFP^-$ recipient cells and transplanted to lethally irradiated recipient mice. After another 4 months, BM was harvested, and chimerism was analyzed as the percentage of $GFP^+$ cells. Despite the increase in phenotypic HSCs and HPCs observed in primary transplants, Gsk3-deficient cells were less efficient in competitive reconstitution than were control cells, as depicted in FIGS. 5B and 5C (see also Table 1, below), with approximately 3-fold fewer functional HSCs in the Gsk3-rnai group.

TABLE I

Functional HSCs are reduced by Gsk3-rnai in competitive repopulation assay

| No. Donor Cells | Vector Control | Gsk3-rnai |
|---|---|---|
| $2 \times 10^4$ | 1/5 | 0/5 |
| $1 \times 10^5$ | 9/12 | 3/12 |
| $5 \times 10^5$ | 10/10 | 10/10 |
| $1 \times 10^6$ | 10/10 | 10/10 |

Cohorts of lethally irradiated mice were transplanted with the indicated numbers of GFP+ vector-control (H1UG) or Gsk3-rnai-transduced bone marrow cells combined with $2 \times 10^5$ host-derived bone marrow cells. The percentage of donor-derived cells in bone marrow was analyzed 16 weeks after reconstitution; greater than 1% donor-derived cells was considered positive engraftment. Values show number of mice with positive engraftment/total mice transplanted. Data from the cohort of mice receiving $1 \times 10^6 GFP+$ cells are also included in FIGS. 5, B and C. The frequency of long-term competitive repopulation units was calculated using Poisson statistics; vector control reconstitution frequency, 1:73,000 (95% confidence interval, 1:54,000-1:100,000); Gsk3-rnai reconstitution frequency, 1:200,000 (95% confidence interval, 1:150,000-1:270,000).

Figures 6A, 6B, 6C, 6D:
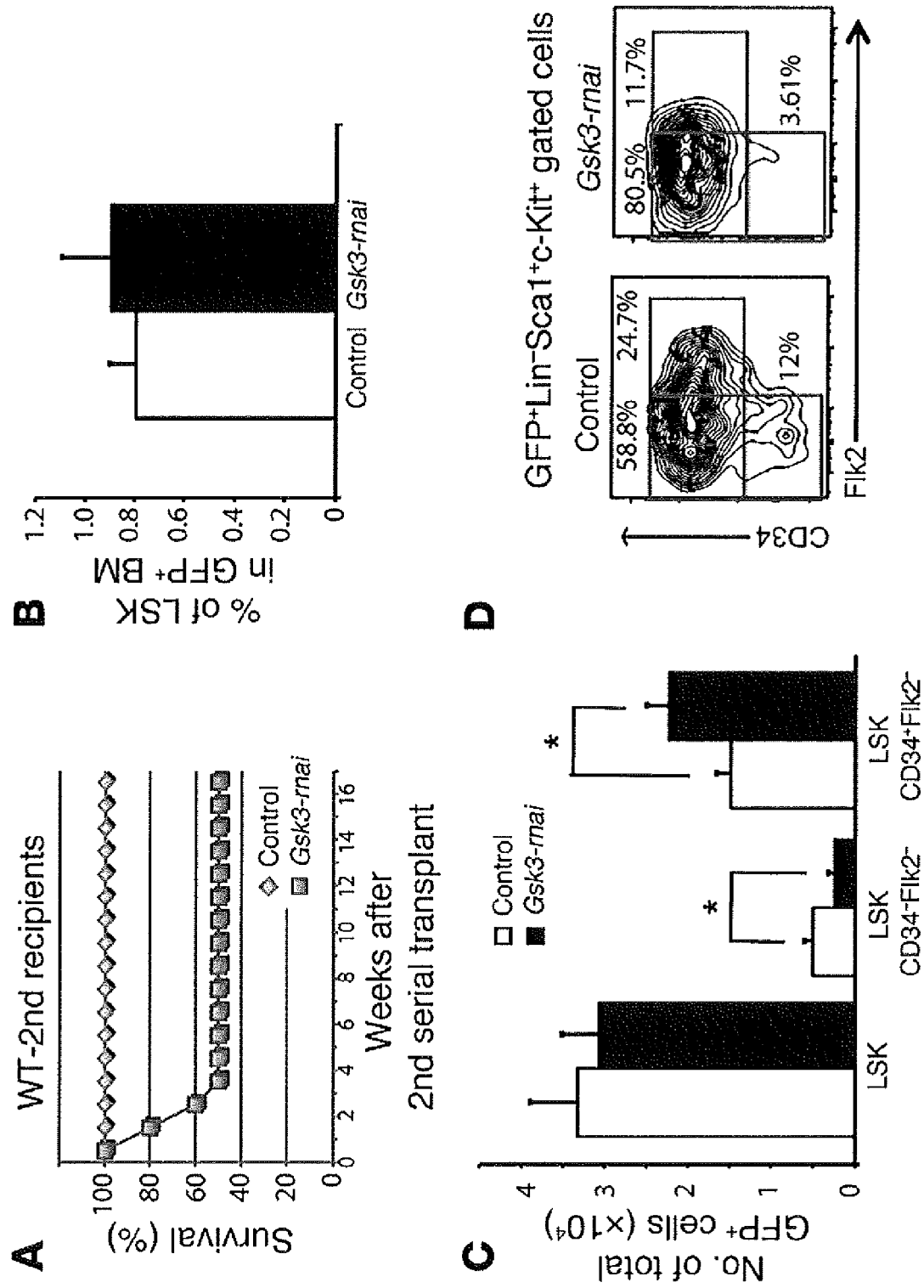
FIG. 6B depicts percent HSC-containing LSK fraction in control and Gsk3-rnai secondary recipients.
FIG. 6C depicts absolute number of GFP$^+$ LSK, LSK CD34$^-$Flk2$^-$, and LSK CD34$^+$Flk2$^-$ cells in control and Gsk3-rnai secondary recipients.
FIG. 6D depicts representative FCM data, presented as the distribution of CD34$^-$Flk2$^-$, CD34$^+$Flk2$^-$, and CD34$^+$Flk2$^-$, which immunophenotypically correspond to LT-HSCs, ST-HSCs, and MPPs in the LSK population, from control and Gsk3-rnai secondary recipients. Percent cells are shown for the indicated gates. As depicted in FIG. 6E, a colony formation assay with sorted GFP$^+$ cells from control and Gsk3-rnai secondary recipient BM was performed and scored as in FIG. 2 using GFP$^+$BM from 5 control and 5 Gsk3-rnai mice. As depicted in FIG. 6F, the frequencies of common myeloid progenitor (CMP), granulocyte-monocyte progenitor (GMP), and megakaryocyte-erythroid progenitor (MEP) cells were measured by detection of CD16/32 and CD34 expression in the lineage$^-$ sca-1$^-$ c-kit$^+$ gated population. The common lymphoid progenitor (CLP) fraction was measured as CD127$^+$ cells in the lineage$^-$sca-1$^{lo}$c-kit$^{lo}$ gate.

As a further test of LT-HSC function, serial, noncompetitive transplantation to secondary and tertiary lethally irradiated hosts was performed. BM was harvested from primary recipients after 4 months, and $2 \times 10^5$ sorted $GFP^+$ cells were transplanted into lethally irradiated secondary recipients. Of recipients of Gsk3-depleted cells, 50% died within 1 month of transplantation, whereas 100% of vector control BM recipients survived, as depicted in FIG. 6A. All control recipients and surviving recipients of Gsk3-rnai-infected cells showed long-term multilineage reconstitution with high levels of $GFP^+$ donor cells contributing to multiple peripheral blood lineages (data not shown) and BM. However, in contrast to primary recipients, BM harvested at 4 months from surviving Gsk3-rnai secondary recipients did not show an increase in $GFP^+$ LSK cells, as depicted in FIG. 6B, or $CD150^+CD48^-$ cells (data not shown), despite the higher number of $GFP^+$ LSK $CD150^+CD48^-$ cells originally present in the Gsk3-rnai donor BM (See FIGS. 2D and 2E). Reduction in GSK-3α and GSK-3β protein was confirmed by Western blot of $GFP^+BM$ cells harvested from secondary recipients after 4 months (data not shown).

Figures 6E, 6F, 6G, 6H:
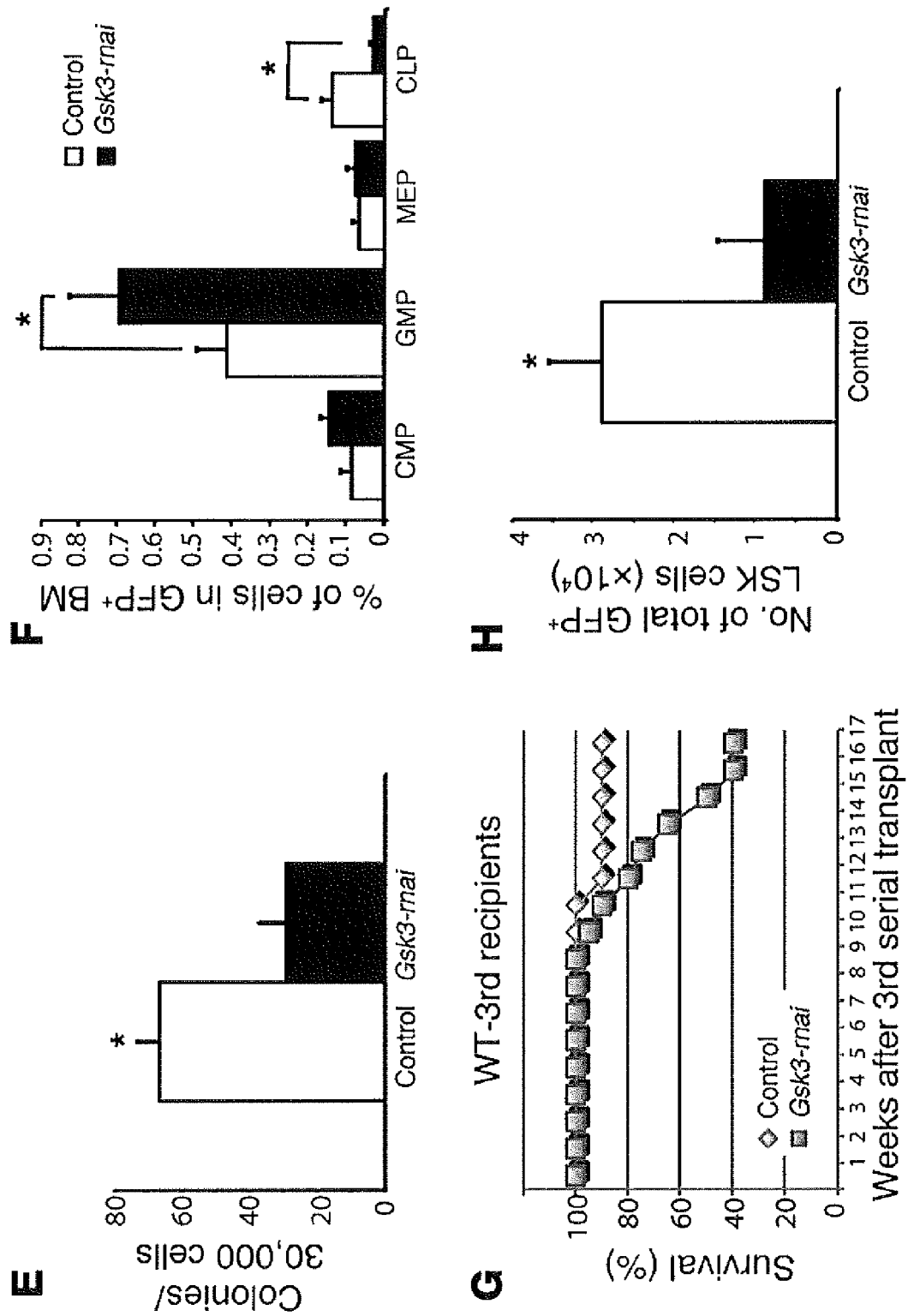
FIG. 6G depicts lethally irradiated mice were reconstituted with 4×10$^5$ sorted GFP$^+$BM cells from secondary recipients of vector or Gsk3-rnai transduced BM. The Kaplan-Meier survival curve shows the survival of tertiary recipients of BM from control or Gsk3-rnai mice.
FIG. 6H depicts absolute number of immunophenotypic HSCs/HPCs, as LSK cells, in control and Gsk3-rnai tertiary recipients. *P<0.05.

Analysis of CD34 and flk-2 further showed that immunophenotypic LT-HSCs were decreased in Gsk3-rnai secondary recipients, and the increase in ST-HSCs (LSK $Flk2^+$ $CD34^+$) was attenuated approximately 2-fold, as depicted in FIGS. 6C and 6D, compared with that in primary recipients (See FIG. 2E). Similarly, colony formation was reduced 2-fold in secondary recipients of Gsk3-rnai compared with vector control, as depicted in FIG. 6E. Furthermore, the proportion of granulocyte-monocyte progenitor cells in the $GFP^+$ population increased, while the percentage of common lymphoid progenitor cells decreased significantly, as depicted in FIG. 6F. These observations suggest that Gsk-3 is required for the maintenance of LT-HSCs and that prolonged loss of GSK-3 activity may promote exit of HSCs from the stem cell pool. To extend this analysis, $GFP^+$ cells recovered from secondary recipients was transplanted to lethally irradiated tertiary recipients, where 12 of 20 mice receiving Gsk3-depleted BM died within 4 months, as depicted in FIG. 6G. LSK cells were reduced 3- to 4-fold in Gsk3-depleted BM in surviving tertiary recipients, as depicted in FIG. 6H, and this marked reduction in HSCs was confirmed by the reduced level of $CD150^+CD48^-$ cells (data not shown). These data indicate that loss of Gsk-3 leads to a progressive decline in HSC function and/or number in the course of long-term serial transplantation. This apparent positive function of Gsk-3 in HSC maintenance was further supported by serial transplantation of HSCs from Gsk3b KO mice (see below).

Example 5

Role of Wnt/β-Catenin Signaling in Response to Gsk-3 Knockdown

Gsk-3 loss-of-function mutations result in stabilization of β-catenin protein and constitutive activation of Wnt signaling (Doble, et al., 2007, Dev. Cell. 12:957-971; Siegfried, et al., 1992, Cell. 71:1167-1179). Thus, the effects of GSK-3 inhibitors or Gsk-3 depletion in HSCs/HPCs could be mediated by activation of downstream Wnt signaling. Wnt signaling is active in HSCs under basal conditions (Trowbridge, et al., 2006, Nat. Med. 12:89-98; Goessling, et al., 2009, Cell. 136: 1136-1147; Reya, et al., 2003, Nature. 423:409-414; Fleming, et al., 2008, Cell Stem Cell. 2:274-283) and is further activated in HSCs isolated from lithium-treated Bat-gal (Maretto, et al., 2003, Proc. Natl. Acad. Sci. U.S.A. 100: 3299-3304) reporter mice (data not shown). Furthermore, β-catenin protein levels were persistently elevated in Gsk3-rnai-infected BM cells, as depicted in FIG. 2C, which suggests that downstream Wnt signaling is activated in these Gsk3-depleted cells.

Figure 7A:
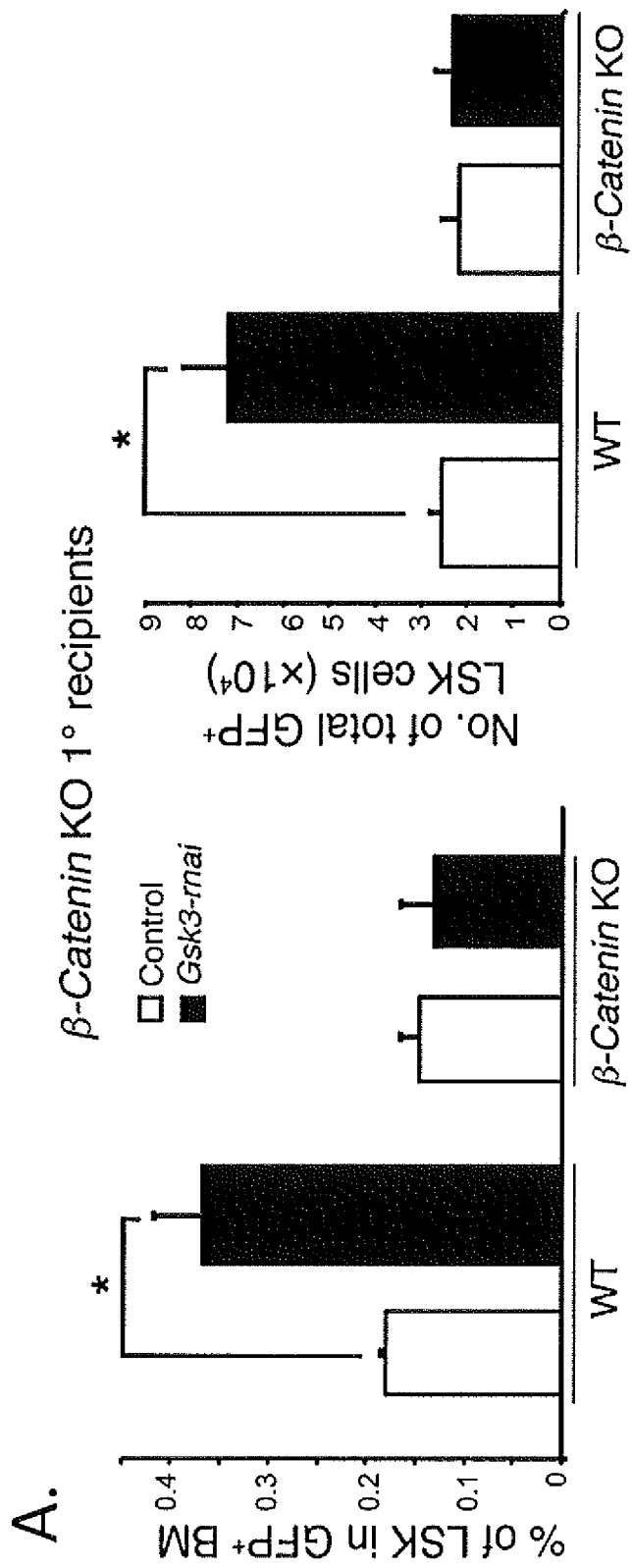
FIG. 7, comprising FIGS. 7A-7C, demonstrates that β-catenin is required for the increase in HSCs/HPCs induced by Gsk3-rnai. As depicted in FIG. 7A, BM cells were harvested from Mx-Cre; β-catenin$^{fl/fl}$ mice with or without injection of polyI:polyC for 14 days, transduced with control or Gsk3-rnai carrying lentivirus, and transplanted into lethally irradiated recipient mice. After 4 months, percentage and absolute number of HSC-containing LSK fraction were compared among the 4 groups. As depicted in FIG. 7B, BM cells were harvested at 4 months from primary recipients of WT and Mx-Cre; β-catenin$^{fl/fl}$ mice transduced with vector control or Gsk3-rnai lentivirus (from primary recipient mice in FIG. 7A) and transplanted into lethally irradiated secondary hosts. After 4 months, percentage and absolute number of HSC-containing LSK fraction were compared among the 4 groups.
FIG. 7C depicts a summary of serial transplantation data in WT versus β-catenin CKO mice. Shown is fold change in GFP$^+$ LSK cells in recipients of Gsk3-depleted BM normalized to vector control, for otherwise WT primary, secondary, and tertiary recipients as well as for primary and secondary β-catenin CKO recipients. Survival in tertiary recipients of Gsk3/β-catenin-deficient BM was too low for statistical significance. *P<0.05.

Although the requirement for Wnt signaling in basal hematopoiesis remains controversial, activation of Wnt signaling can enhance HSC self renewal and HPC function in vivo and ex vivo (Trowbridge, et al., 2006, Nat. Med. 12:89-98; Goessling, et al., 2009, Cell. 136:1136-1147; Austin, et al., 1997, Blood. 89:3624-3635; Van Den Berg, et al., 1998, Blood. 92:3189-3202; Willed, et al., 2003, Nature. 423:448-452; Reya, et al., 2003, Nature. 423:409-414; Baba, et al., 2006, J. Immunol. 177:2294-2303). It was therefore tested whether β-catenin is required for the effects of Gsk-3 depletion on hematopoiesis using a conditional β-catenin loss-of-function allele (β-catenin$^{fl/fl}$) crossed to interferon-inducible Mx-cre mice (Cobas, et al. 2004, J. Exp. Med. 199:221-229). Cre was induced in Mx-cre; β-catenin$^{fl/fl}$ mice with polyinosine-polycytidine (polyI:polyC), and BM was harvested and infected with control or Gsk3-rnai lentivirus. After infection, cells were transplanted to lethally irradiated hosts, and after 4 months, BM from these primary recipients was harvested and analyzed by FCM. Depletion of Gsk-3 increased the number of GFP$^+$ LSK cells (as well as CD150$^+$CD48$^-$ cells) derived from WT hosts, and loss of β-catenin blocked this effect in primary recipients, as depicted in FIG. 7A. In addition, β-catenin$^{fl/fl}$ conditional KO (CKO) blocked the increase in colony formation observed in Gsk3-rnai; β-catenin$^{+/+}$BM (compare FIG. 8 and FIG. 2H), demonstrating that β-catenin is required for the effect of Gsk-3 depletion in primary transplanted HSCs/HPCs.

Figures 7B, 7C:
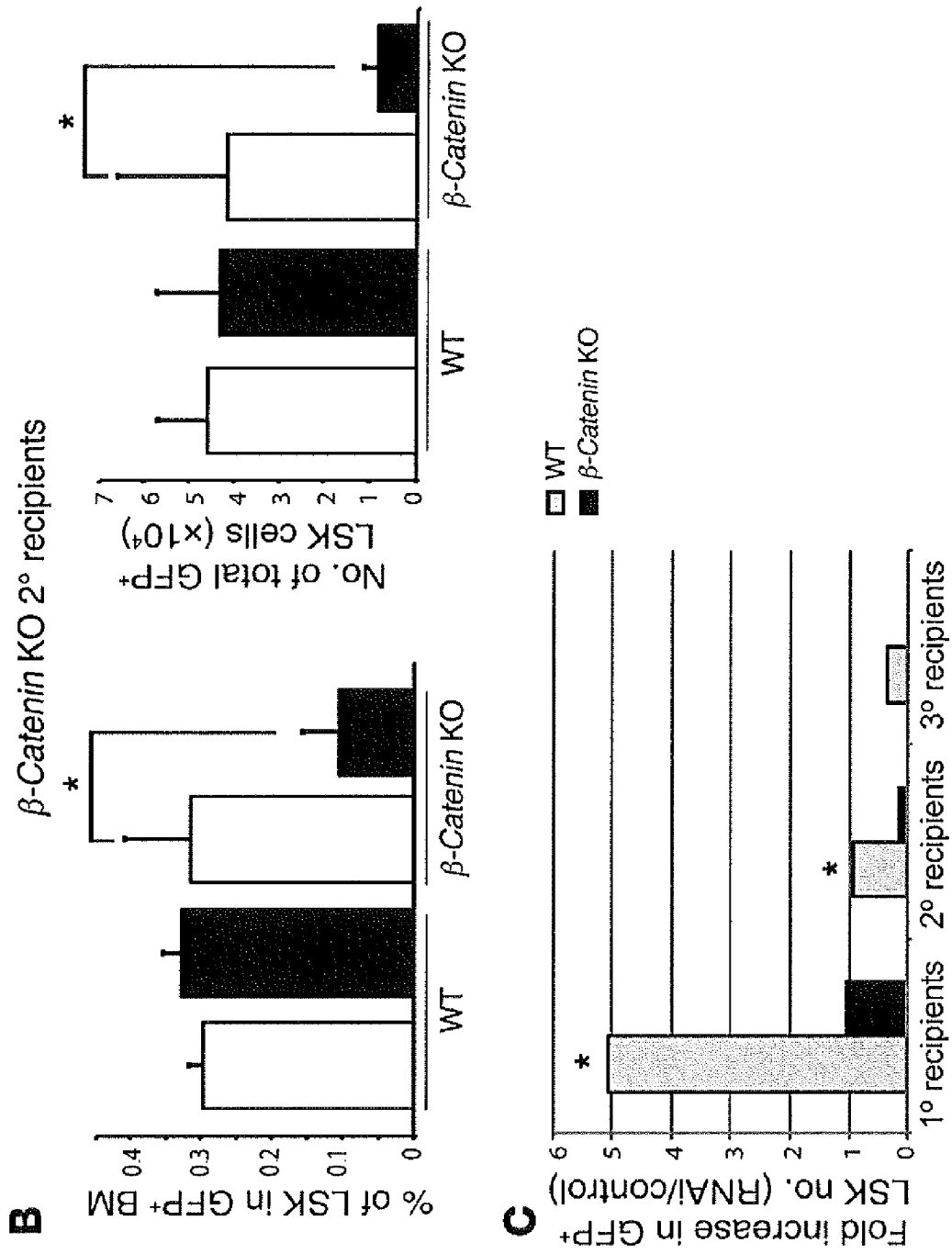

BM from Gsk3-rnai, WT, and β-catenin CKO primary recipients was also transplanted to secondary lethally irradiated recipients. As with Gsk3-rnai; β-catenin$^{+/+}$BM, transplantation of Gsk3-rnai; β-catenin$^{fl/fl}$ CKO BM resulted in reduced survival. After 4 months, BM was harvested, and LSK cells were measured within the GFP$^+$ population. Loss of β-catenin resulted in a 3-fold reduction in LSK cells after secondary transplantation of Gsk3-depleted BM, as depicted in FIG. 7B. BM from each group of secondary recipients was also transplanted to tertiary recipients, but the survival of Gsk3-rnai; β-catenin$^{fl/fl}$ recipients at 4 months was too low for analysis (data not shown). The serial BM from WT and β-catenin CKO transplantation data, also summarized in FIG. 7C, demonstrate that β-catenin contributes to HSC maintenance throughout successive transplants of Gsk3-deficient BM cells. These data, taken together with previously published observations from others (Goessling, et al., 2009, Cell. 136:1136-1147; Austin, et al., 1997, Blood. 89:3624-3635; Van Den Berg, et al., 1998, Blood. 92:3189-3202; Willert, et al., 2003, Nature. 423:448-452; Reya, et al., 2003, Nature. 423:409-414; Jeannet, et al., 2008, Blood, 111:142-149; Baba, et al., 2006, J. Immunol. 177:2294-2303; Zhao, et al., 2007, Cancer Cell. 12:528-541; Luis, et al., 2009, Blood. 113:546-554; Fleming, et al., 2008, Cell Stem Cell. 2:274-283), support a positive role for the Wnt/β-catenin pathway in HSC maintenance in the context of reduced GSK-3 activity, but also suggest that an additional GSK-3-regulated pathway plays a distinct and possibly antagonistic role in HSC maintenance.

Example 6 mTOR Inhibition Expands HSCs in Gsk3-Deficient BM

Figures 9A, 9B, 9C, 9D:
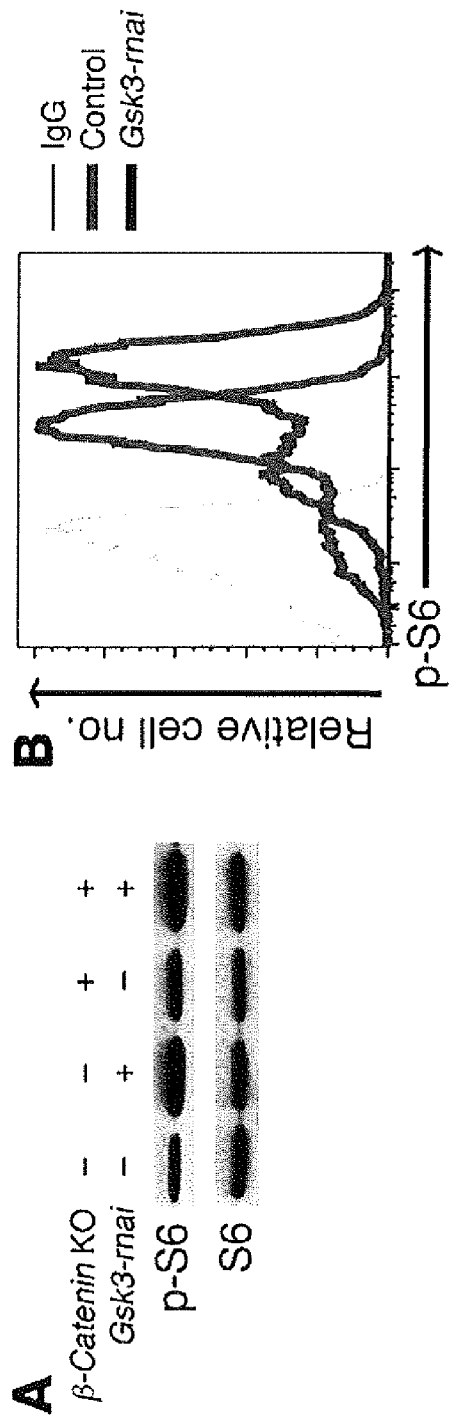
FIG. 9B depicts flow cytometric detection of phospho-ribosomal protein S6 with BM cells in FIG. 9A. As depicted in FIG. 9C, irradiated mice were reconstituted with BM transduced with control vector or Pten-rnai. After 4 months, phospho-GSK-3 and phospho-ribosomal protein S6 were assessed in GFP$^+$ cells by immunoblot. As depicted in FIG. 9D, NIH3T3 cells were infected for 3 days with control or Pten-rnai lentivirus, and phospho-GSK-3α/β in control and Pten-depleted cells was detected by immunoblot.

Although GSK-3 regulates multiple pathways, the initial expansion and subsequent depletion of phenotypic HSCs—as well as the reduction in functional HSCs—observed with Gsk-3 knockdown was strikingly similar to the hematopoietic phenotype previously reported for Pten KO mice (Yilmaz, et al., 2006, Nature. 441:475-482; Zhang, et al., 2006, Nature. 441:518-522). PTEN is a negative regulator of the PI3K/Akt pathway and maintains GSK-3 activity by antagonizing Akt-dependent phosphorylation of GSK-3. Pten CKO within HSCs activates the mTOR pathway, and the transient expansion and subsequent depletion of HSCs in Pten KO cells can be rescued by treatment of mice with the mTOR inhibitor rapamycin. However, the mechanism for PTEN suppression of mTOR activity has not been fully elucidated. GSK-3 was recently shown to inhibit mTOR signaling through phosphorylation of Tsc2, which, together with Tsc1, antagonizes mTOR signaling (Inoki, et al., 2006, Cell. 126:955-968). Furthermore, deletion of Tsc1 increases proliferation and reduces self renewal of HSCs, similar to loss of Pten (Chen, et al., 2008, J. Exp. Med. 205:2397-2408; Gan, et al., 2008, Proc. Natl. Acad. Sci. U.S.A. 105:19384-19389) and reduced Gsk-3 expression. Thus, it is believed that the reduction in HSCs in Gsk3-depleted BM is caused by activation of mTOR. To test this Western blotting and FCM were used to examine phosphorylation of ribosomal protein S6, a marker for activation of mTOR, in Gsk3-deficient and control BM. S6 phosphorylation was modestly increased in primary recipients of Gsk3-rnai BM (data not shown) and more demonstrably increased in secondary recipients, as depicted in FIGS. 9A and 9B). S6 phosphorylation was not affected by deletion of β-catenin in either primary or secondary recipients.

These observations suggest that GSK-3 is a downstream target of PTEN-regulated pathways in hematopoietic cells. To test this directly, expression of Pten in BM cells was reduced by lentivirally mediated RNAi and harvested BM from primary hosts after 4 months. The inhibitory phosphorylation of GSK-3β (serine-9) increased, as depicted in FIG. 6C, which was consistent with reduced PTEN activity and increased Akt-mediated GSK-3β phosphorylation. Knockdown of Pten in NIH-3T3 cells also increased phosphorylation of GSK-3β, as depicted in FIG. 9D. These data indicate that GSK-3β is indeed a downstream target of PI3K/PTEN regulation in hematopoietic cells.

Figures 9E, 9F, 9G, 9H:
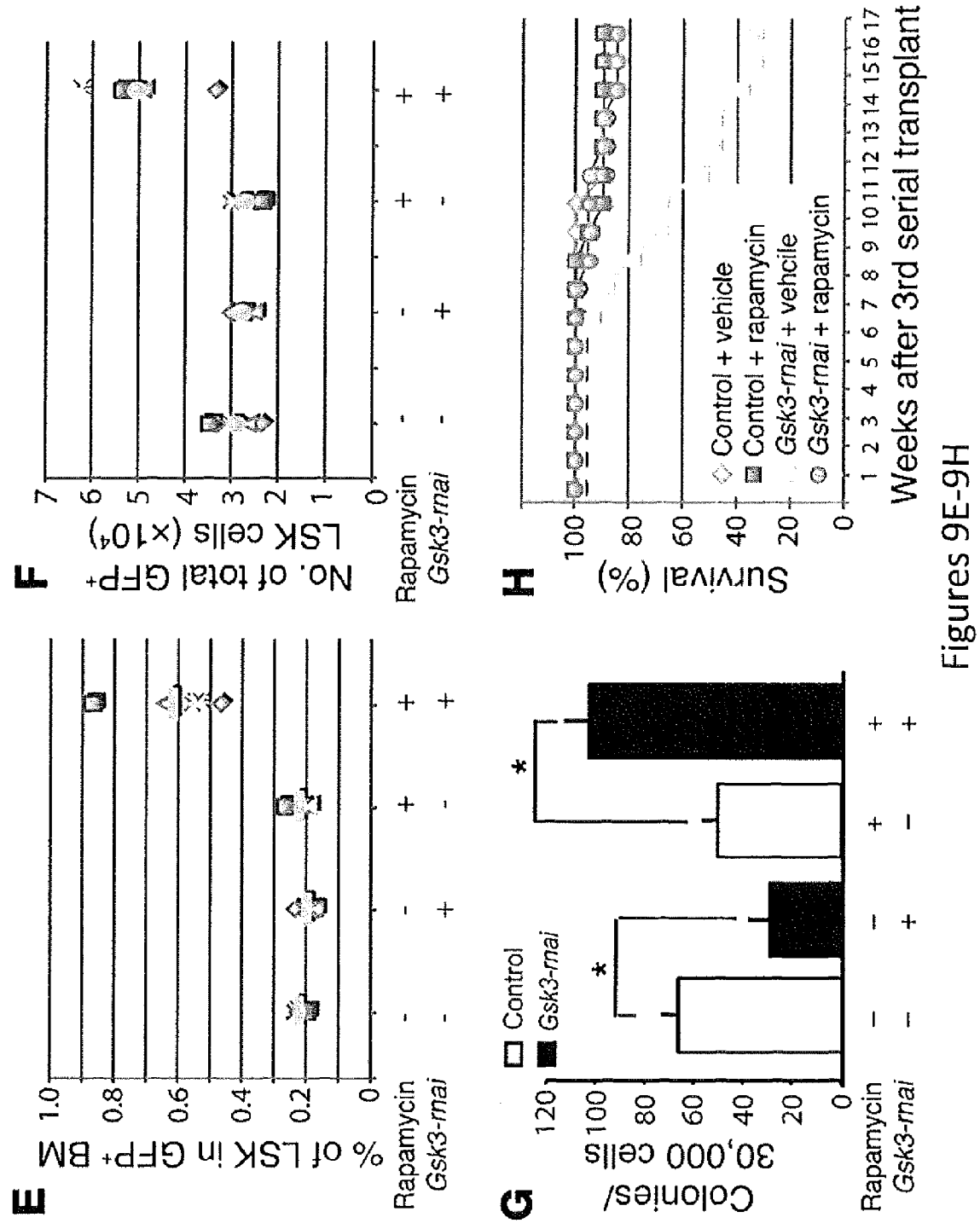
FIG. 9E depicts increased percentage of LSK cells in bone marrow of 2° recipients of Gsk3-depleted BM that were treated with rapamycin for 8 weeks. GFP$^+$ cells ($2 \times 10^6$) from primary recipients of control or Gsk3-rnai were transplanted into 10 irradiated recipients per group. After 1.5-2 months, secondary recipients were injected with rapamycin or vehicle every other day for 8 weeks. Percent GFP$^+$ LSK cells was compared among the 4 groups.
FIG. 9F depicts absolute number of GFP$^+$ LSK cells as in FIG. 9E.
FIG. 9G depicts colony formation with sorted GFP$^+$ cells from FIG. 9E.
FIG. 9H depicts a Kaplan-Meier plot showing survival of tertiary recipients transplanted with BM from control- and rapamycin-treated secondary recipients in FIGS. 9E-9G. Illustrated is control vector BM from secondary recipients treated with vehicle or rapamycin and Gsk3-rnai-infected BM from secondary recipients treated with vehicle or rapamycin transplanted to lethally irradiated tertiary recipients. *P<0.05.

Next, secondary recipients of Gsk3-rnai and control BM were treated with rapamycin, as this prevents HSC depletion in Pten KOs (Yilmaz, et al., 2006, Nature. 441:475-482). Rapamycin restored the LSK population in secondary recipients of Gsk3-depleted BM, with a 3- to 4-fold increase in LSK cells, compared with vehicle-injected controls, as depicted in FIGS. 9E and 9F, which suggests that Gsk-3 depletion increases the HSC population above baseline, perhaps through activation of Wnt/β-catenin signaling in the absence of the antagonistic influence of mTOR signaling in HSCs. Colony formation also increased 2- to 3-fold in BM harvested from rapamycin-treated Gsk3-rnai recipients, as depicted in FIG. 9G, further demonstrating that rapamycin rescues the effect of Gsk3-rnai in secondary recipients. Furthermore, rapamycin treatment also rescued survival of tertiary recipients of Gsk3-depleted BM, as depicted in FIG. 6H, which indicates that inhibition of mTOR preserves LT-HSCs in Gsk3-depleted BM. However, it will be important in future work to measure the number of functional HSCs after treatment with rapamycin using competitive repopulation assays.

Example 7

Gsk3b is Required for Maintenance of the HSC-Enriched LSK Cell Population

Figure 10:
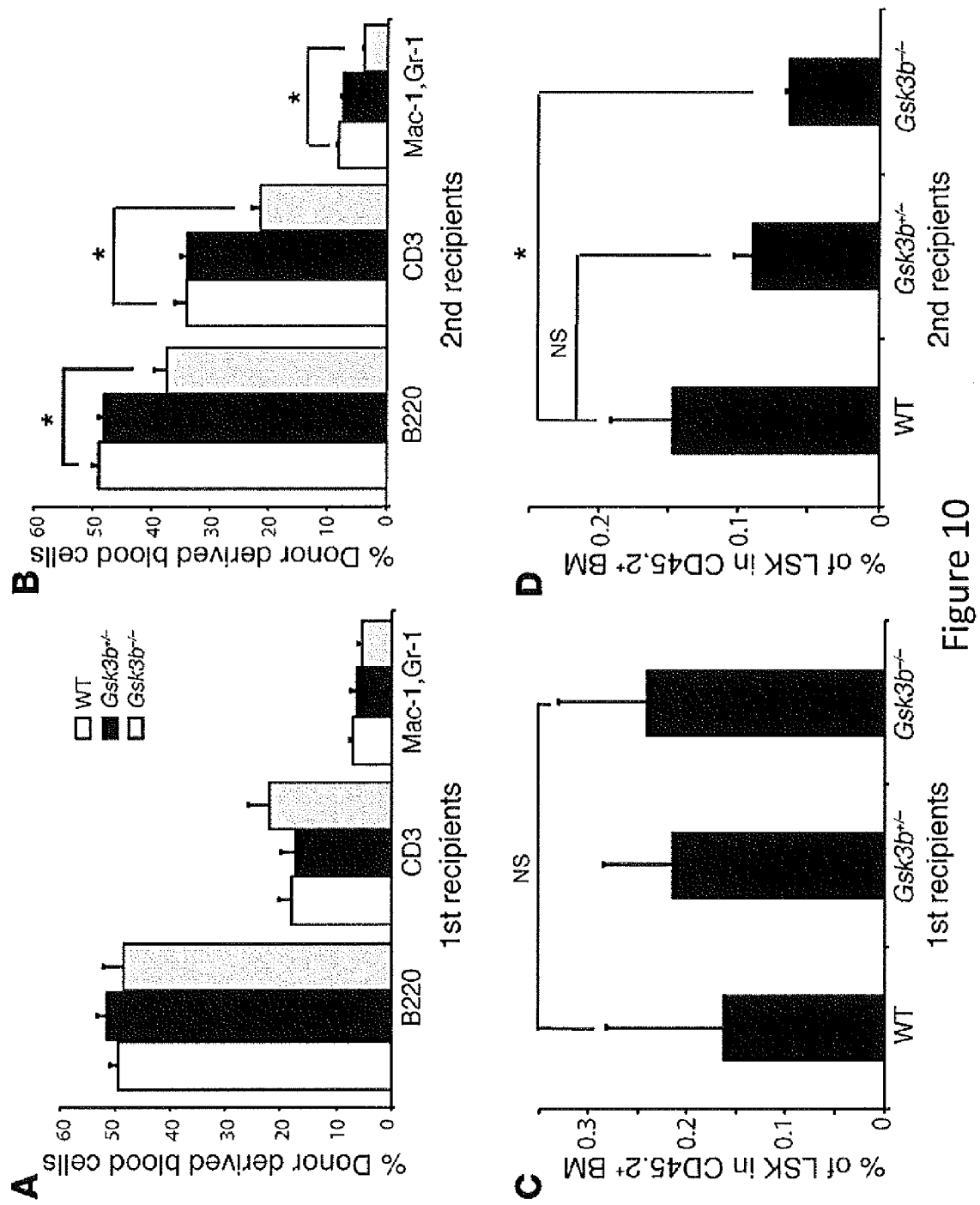
FIG. 10, comprising FIGS. 10A-10D, demonstrates that Gsk3b KO depletes HSCs in serial BM transplants. Noncompetitive serial transplants were performed by transplanting $4 \times 10^5$ fetal liver cells (CD45.2) from E17.5 WT, Gsk3b$^{+/-}$, and Gsk3b$^{-/-}$ embryos into lethally irradiated recipient mice (CD45.1).

Surprisingly, reduced expression of Pten had little effect on phosphorylation of GSK-3α, as depicted in FIG. 9D, raising the possibility that GSK-3β is a specific target of PI3K/PTEN regulation in HSCs. Although Gsk3a and Gsk3b are structurally similar and are clearly redundant in Wnt signaling (Doble, et al., 2007, Dev. Cell. 12:957-971), the 2 genes are not redundant in all contexts (Hoeflich, et al., 2000, Nature. 406:86-90; MacAulay, et al., 2007, Cell Metab. 6:329-337). To test the specific role of Gsk3b in HSC maintenance, transplants were performed with hematopoietic cells derived from Gsk3b$^{-/-}$ embryos, which express WT levels of Gsk3a. Homozygous loss of Gsk3b in mice is lethal between 15 and 18 days of gestation (Hoeflich, et al., 2000, Nature. 406:86-90). Thus, fetal liver cells were harvested from E17.5 WT, Gsk3b$^{+/-}$, and Gsk3b$^{-/-}$ embryos and transplanted into lethally irradiated adult mice. After 4 months, recipients of WT, Gsk3b$^{+/-}$, and Gsk3b$^{-/-}$ BM showed long-term multilineage reconstitution derived from donor cells, as depicted in FIGS. 10A and 10B. However, there was no significant increase in the percentage or absolute number of LSK or CD150$^+$CD48$^-$ cells in primary hosts receiving Gsk3b$^{-/-}$ fetal liver cells, as depicted in FIG. 10C. This lack of increase in HSCs in primary recipients with selective loss of Gsk3b is in contrast to RNAi-mediated knockdown of both Gsk3a and Gsk3b. Because the increase in HSCs after Gsk-3 depletion required β-catenin, this observation is consistent with the well-established redundant roles for Gsk3a and Gsk3b in Wnt signaling (Doble, et al., 2007, Dev. Cell. 12:957-971). However, in secondary transplant recipients, Gsk3b$^{-/-}$ donor cells demonstrated a 3- to 4-fold reduction in LSK cells compared with WT cells, as depicted in FIG. 10D, which suggests that Gsk3b regulates HSC homeostasis through a Wnt/β-catenin-independent pathway that becomes evident in secondary transplants and is not compensated for by Gsk3a. Although the respective roles of Gsk3a and Gsk3b may differ in fetal versus adult HSCs, these observations, taken together with the selective phosphorylation of GSK-3β when Pten expression is reduced in hematopoietic cells (or in fibroblasts), suggest that GSK-3β is a selective target of PTEN-regulated pathways and is required for the maintenance of HSC self renewal.

Figure 11:
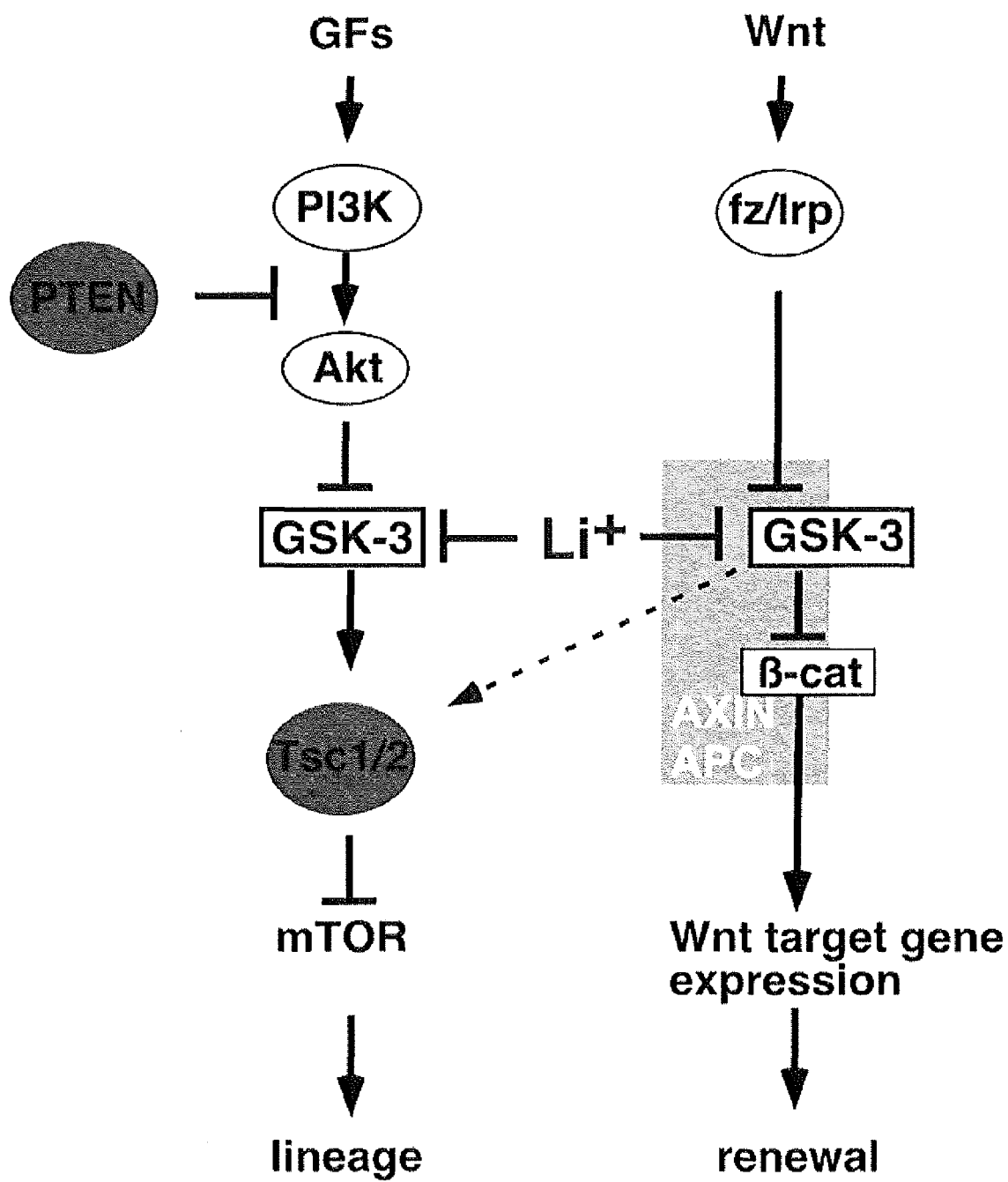
FIG. 11 demonstrates that GSK-3 functions in 2 major pathways to regulate HSC self renewal and lineage commitment. Inhibition of GSK-3 activates Wnt and mTOR signaling. In the canonical Wnt pathway, GSK-3 and β-catenin bind to the Axin complex, along with APC. GSK-3 phosphorylates β-catenin, targeting it for rapid destruction. Wnt binding to the Fz/Lrp receptor complex causes inhibition of GSK-3, which in turn stabilizes β-catenin and activates Wnt target genes that promote progenitor proliferation and self renewal. In PI3K/PTEN-regulated pathways, growth factors (GFs) bind to surface receptors and activate PI3K, leading to activation of Akt, whereas PTEN inhibits activation of Akt. Once activated, Akt phosphorylates and inhibits GSK-3. GSK-3 phosphorylates Tsc2, inhibiting the mTOR pathway. Thus, inhibition of GSK-3 activates mTOR and promotes proliferation and exit from the LT-HSC pool. Inhibition of GSK-3 thus activates distinct downstream signaling pathways that have opposing functions in HSC renewal and differentiation.
Figure 12:
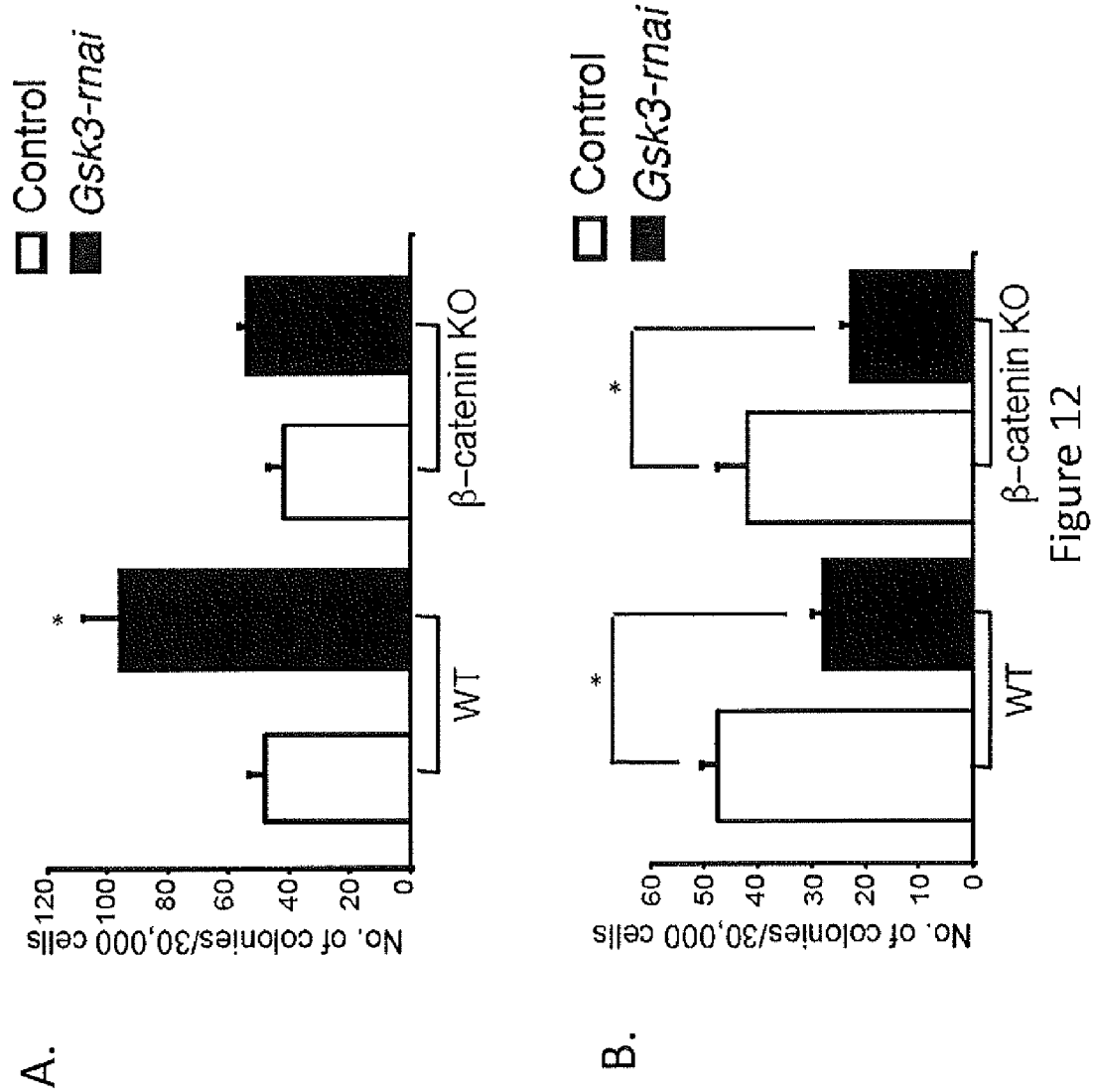
FIG. 12, comprising FIGS. 12A and 12B, demonstrates the effect of β-catenin conditional knockout on colony formation in Gsk3-depleted bone marrow. A colony formation assay was performed using sorted GFP+ cells from each group in 1° (FIG. 12A) and 2° (FIG. 12B) recipients. Data represent mean number of colonies per well for five mice per construct repeated in three separate experiments.

As demonstrated herein, Gsk-3 plays an essential role for in the maintenance of LT-HSCs. Gsk-3 loss of function phenocopies Pten and Tsc1 mutations in HSCs/HPCs, supporting the belief that GSK-3 functions downstream of PTEN to suppress mTOR-dependent HSC activation and lineage commitment. However, inhibition of GSK-3 also stabilizes β-catenin within HSCs/HPCs to induce a β-catenin-dependent increase in phenotypic HSCs, and β-catenin KO accelerates the loss of LT-HSCs in Gsk3-depleted BM, consistent with prior reports with activators of Wnt signaling (Austin, et al., 1997, Blood. 89:3624-3635; Van Den Berg et al., 1998, Blood. 92:3189-3202; Willert et al. 2003, Nature. 423:448-452; Reya, et al., 2003, Nature. 423:409-414; Baba, et al., 2006, J. Immunol. 177:2294-2303; Fleming, et al., 2008, Cell Stem Cell. 2:274-283). Thus, as depicted in FIG. 11, Gsk-3 functions in at least two apparently opposing processes within HSCs/HPCs. This indicates that Gsk-3 plays an essential role in regulating the balance between self renewal and lineage commitment in HSC, and also supports the belief that the highly prevalent effects of lithium on hematopoiesis in bipolar patients are mediated by inhibition of GSK-3, and suggest a therapeutic approach, using currently approved GSK-3 and mTOR inhibitors, to expand HSCs in vivo.

Figure 8:
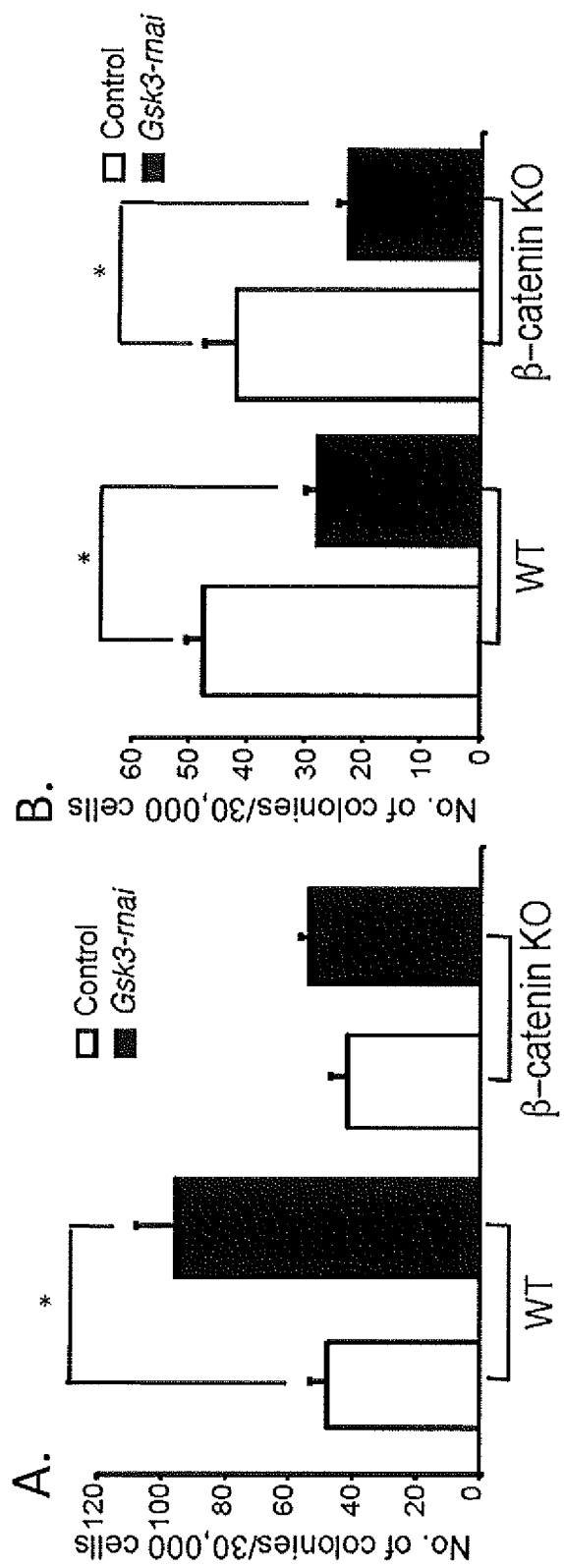
FIG. 8, comprising

Pten KO in HSCs/HPCs leads to activation and subsequent depletion of HSCs, increased lineage commitment resembling myeloproliferative disorder, and leukemia (Yilmaz et al., 2006, Nature. 441:475-482; Zhang, et al., 2006, Nature. 441:518-522), and this is prevented by the mTOR inhibitor rapamycin, which suggests that PTEN-mediated suppression of mTOR is required for maintenance of quiescent HSCs. Similarly, deletion of the mTOR inhibitor Tsc1 shifts HSCs from a quiescent to a proliferative state and reduces HSC self renewal (Chen, et al., 2008, J. Exp. Med. 205:2397-2408; Gan, et al., 2008, Proc. Natl. Acad. Sci. U.S.A. 105:19384-19389). As demonstrated herein, reduced expression of Gsk-3, either through RNAi or by homozygous Gsk3b KO, yielded a similar hematopoietic phenotype. This Gsk-3 phenotype was also reversed by rapamycin, and GSK-3β phosphorylation increased in Pten-depleted BM, which suggests that GSK-3β functions downstream of PTEN to antagonize mTOR activation and maintain stem cell self renewal. In support of this, GSK-3 has previously been shown to antagonize mTOR activation in HEK293T cells by phosphorylating Tsc2 (Inoki, et al., 2006, Cell. 126:955-968). Interestingly, that work showed that Wnts could activate mTOR by inhibiting GSK-3, suggesting a bifurcation of the canonical Wnt pathway that could activate distinct and potentially opposing processes, as depicted in FIG. 8. Furthermore, very recent work suggests that Wnt signaling through mTOR may also cause epidermal stem cell exhaustion, and this can also be prevented by rapamycin (Castilho, et al., 2009, Cell Stem Cell. 5:279-289). Although it is not yet known whether Wnts activate mTOR in HSCs/HPCs, activation of both mTOR- and β-catenin-dependent processes could explain some of the conflicting reports on Wnt effects in hematopoiesis (Staal, et al., 2008, Eur. J. Immunol. 38:1788-1794; Malhotra, et al., 2009, Cell Stem Cell. 4:27-36), if differing experimental conditions bias the effects toward either mTOR- or β-catenin-dependent responses.

Although the Gsk-depletion phenotype was similar to the Pten KO, important differences should also be noted. Conditional deletion of Pten (or Tsc1) leads to rapid HSC exhaustion, whereas the reduction in HSCs observed with Gsk3-rnai became evident more slowly, through serial transplants and competitive repopulation assays. Indeed, the initial expansion in phenotypic HSCs was observed 4 months after primary transplant; the number of phenotypic HSCs declined to control levels in secondary recipients, and only fell below control levels in tertiary transplants, as depicted in FIG. 10C. It is believed that the delay is because the activation of HSCs and their subsequent exit from the HSC pool are balanced by enhanced Wnt signaling, which would slow the rate of HSC activation and depletion, ad depicted in FIG. 11; this idea is supported by the more rapid decline in phenotypic HSCs in Gsk3-rnai; β-catenin KO BM. Pten deletion also leads to leukemia in a substantial fraction of animals, which has not been observed so far with the Gsk3-rnai-transplanted mice. However, PTEN regulates multiple downstream effectors in addition to GSK-3, and modulation of these pathways could contribute to the Pten HSC phenotype independently of GSK-3 function. It is also possible that the acute leukemia observed in Pten KO mice is blocked in mice expressing nonphosphorylatable mutants of Gsk-3.

It was found that β-catenin was required for the initial increase in phenotypic HSCs/HPCs in response to Gsk-3 inhibition and for the maintenance of Gsk3-depleted HSCs in long-term transplant assays. These observations are consistent with previous studies showing that activation of canonical Wnt signaling can promote HSC self renewal and proliferation ex vivo (Austin, et al., 1997, Blood, 89:3624-3635; Van Den Berg, et al., 1998, Blood. 92:3189-3202; Willert, et al., 2003, Nature. 423:448-452; Reya, et al., 2003, Nature. 423:409-414; Baba, et al., 2006, J. Immunol. 177:2294-2303; Fleming, et al., 2008, Cell Stem Cell. 2:274-283). Although basal hematopoiesis was unaffected when β-catenin was deleted in adult BM, consistent with previous reports (Cobas, et al., 2004, J. Exp. Med. 199:221-229; Koch, et al., 2008, Blood. 111:160-164), inhibition of Gsk-3 can be considered a Wnt gain of function. The issue of whether canonical Wnt signaling is required for basal HSC homeostasis remains controversial (Staal, et al., 2008, Eur. J. Immunol. 38:1788-1794; Malhotra, et al., 2009, Cell Stem Cell. 4:27-36). A recent report showed that canonical Wnt signaling can function in HSCs in the absence of β-catenin (Jeannet, et al., 2008, Blood. 111:142-149), which suggests that loss of β-catenin does not necessarily block all Wnt signaling. In addition, conditional deletion of p-catenin with cre recombinase driven by the vav promoter impairs LT-HSC self renewal (Zhao, et al., 2007, Cancer Cell. 12:528-541). As vav expression begins in utero, whereas Mx-cre was used to delete β-catenin in adult BM (present disclosure; Cobas, et al., 2004, J. Exp. Med. 199:221-229; Koch, et al., 2008, Blood. 111:160-164), a reasonable explanation for these differences is that the role of Wnt/β-catenin signaling in basal hematopoiesis depends on the developmental context. In support of an early requirement for Wnt signaling in developing HSCs, long-term reconstituting capacity in serial transplants is impaired in HSCs recovered from fetal liver of Wnt3a KO embryos (Luis, et al., 2009, Blood. 113:546-554).

Lithium's effects on hematopoiesis have been known for decades and affect more than 90% of patients taking it, yet the mechanism of lithium action in this setting had not previously been defined. Plausible targets of lithium in addition to GSK-3 include inositol monophosphatase, which may indirectly regulate inositol trisphosphate signaling, and related phosphomonoesterases that play important roles in cell metabolism (York, et al., 2001, Adv. Enzyme Regul. 41:57-71; Gurvich et al., 2002, Pharmacol. Ther, 96:45-66). Therefore, a priori, it should not be considered obvious that GSK-3 is the biologically relevant target of lithium in HSCs, and it is essential to validate GSK-3 as the target in this setting. In support of this hypothesis, structurally diverse GSK-3 inhibitors mimicked lithium effects on the HSC pool and on progenitor cells (FIG. 1; Trowbridge, et al., 2006, Nat. Med. 12:89-98; Goessling, et al., 2009, Cell. 136:1136-1147; Holmes, et al. 2008, Stem Cells. 26:1288-1297). Importantly, depletion of Gsk3a and Gsk3b mimics lithium action in HSCs and HPCs as well as more differentiated myeloid cells. Although these observations suggest that targeting GSK-3 may be a fruitful approach to treating hypoproliferative hematopoietic disorders, the reduction in LT-HSCs with Gsk-3 loss of function suggests this should be approached with caution. Lithium has, in fact, been tested in clinical trials to enhance hematopoietic recovery after myelosuppressive chemotherapy, but this approach has not seen wide use, perhaps in part because of the risk of lithium side effects in already critically ill patients, but also because of limited success in restoring hematopoiesis in patients with reduced numbers of HSCs. It is also possible that the 0-catenin-dependent increase in HSCs in response to lithium is offset by activation of mTOR and exit from the HSC pool, which would be consistent with the increase in more differentiated hematopoietic cells (especially those of myeloid lineage) commonly observed with lithium. As described herein, the combination of lithium and rapamycin in accordance with the present invention, both of which are now in wide clinical use, may achieve a more marked and durable increase in HSCs.

Example 8

Expansion of HSCs Using Gsk-3 and mTOR Inhibitors and Transplantation

It was further determined whether the expansion of HSCs exposed to at least one GSK-3 inhibitor and at least one mTOR inhibitor increased the success of HSC transplants. First, bone marrow cells were harvested from SJL (CD45.1+) mice. The red blood cells were lysed, and s-kit positive cells were purified to enrich hematopoietic stem and progenitor cells (HSCs and HPCs). c-kit+ cells were purified according to established purification protocols and cultured in 12 well plates in (X-vivo15) medium with about 5 mM LiCl and about 5 nM rapamycin for 7 days. No cytokines or other growth factors were added, and no serum was added. Controls included no drug added and single treatment (LiCl alone or rapamycin alone) controls. All cells from one well were divided into three groups and transplanted to 3 lethally irradiated congenic recipients (B6/CD45.2).

The transplant recipients that received c-kit+ cells cultured for 7 days (without added drugs) died within 14 days, similar to known controls for recipients not transplanted with bone marrow. Transplant recipients that received c-kit+ cells cultured for seven days (with LiCl) died within 18 to 19 days. Significantly, 5/6 recipients of the c-kit+ cells treated with LiCl and rapamycin survived up to six weeks, suggesting successful, durable transplant. This indicates expansion of short-term HSCs, long-term HSCs, or both. Importantly, the transplanted cells contribute greater than 60% of peripheral blood, including myeloid and T and B cells, at 5 to 6 weeks post transplant.

Thus, it is demonstrated herein the dual functions of GSK-3 within hematopoietic cells. GSK-3 antagonizes the canonical Wnt pathway, and inhibition of GSK-3 activated the pathway to enhance HSC self renewal. This response to GSK-3 inhibition required β-catenin, as phenotypic HSCs were reduced in 0-catenin CKO BM in both primary and secondary transplant recipients of Gsk3-depleted BM. GSK-3 also antagonizes mTOR signaling, and inhibition of Gsk-3 either by RNAi or by conventional gene KO activated mTOR (similar to Pten or Tsc1 KOs) and led to activation of HSCs, with an initial expansion of LSK cells followed by dramatic depletion of HSCs (as assessed by long-term reconstitution assays). Thus, the combination of lithium and rapamycin can be used to expand HSCs either in vivo or ex vivo in HSC transplants, in the therapy of hypoproliferative hematologic diseases, and any other such use as described herein.

Example 9

Figure 13:
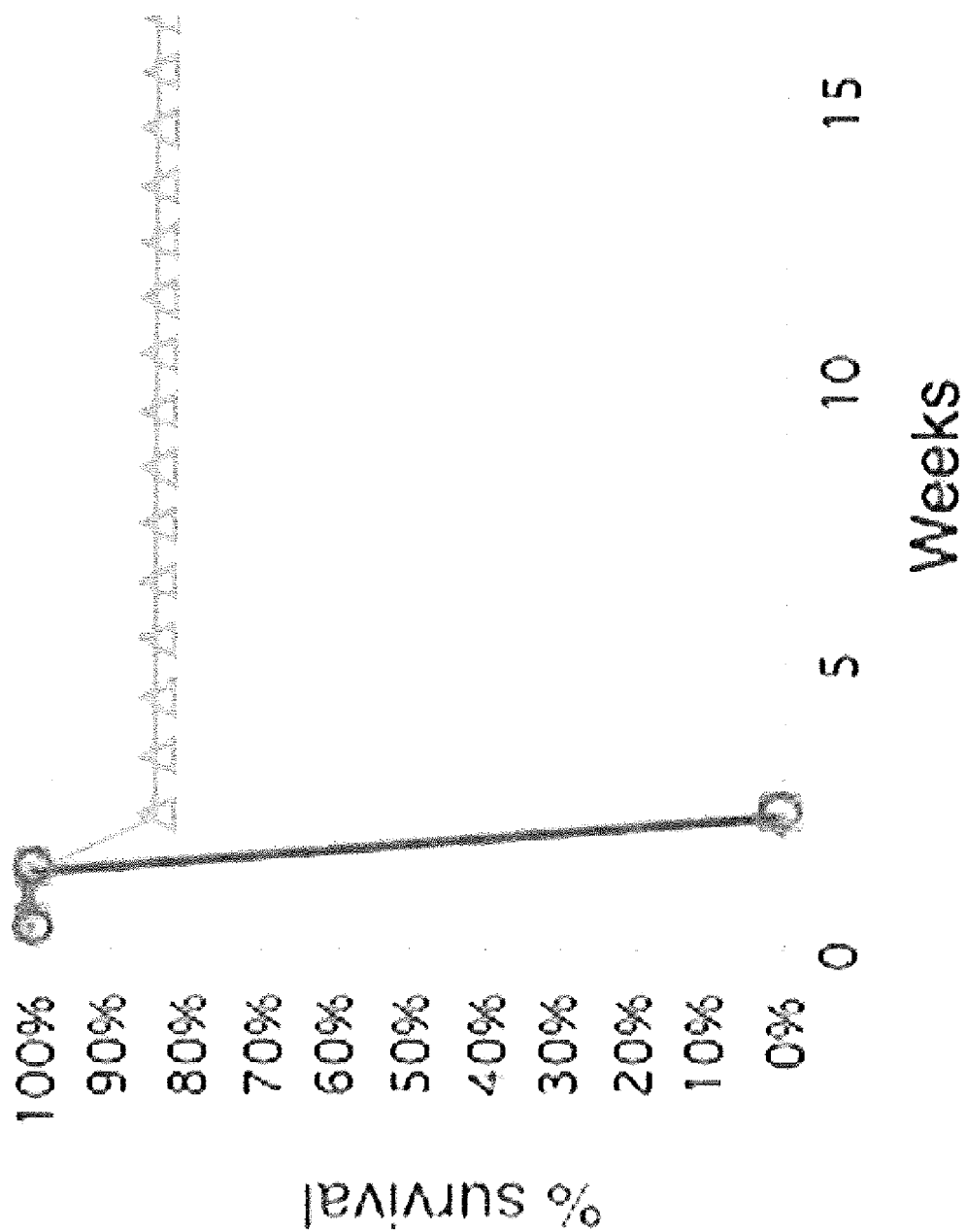
FIG. 13 demonstrates ex vivo mouse HSC culturing and transplantation. c-kit+ cells were isolated from adult mouse bone marrow and cultured in serumfree, cytokine-free defined medium for 7 days with (triangle) or without (circle) our formulation. After 7 days, the entire culture was transplanted to lethally irradiated mice (5/group) and survival was monitored over more than 16 weeks. All control animals (cultured without additives or no transplant) died within 17 days. Mice receiving bone marrow cells cultured in cytokine-free, serum-free medium with additives survived over 16 weeks. The experiment has been repeated 3 times. Erythrocytic, myelocytic, lymphocytic, and megakaryocytic lineages were present in peripheral blood and bone marrow after 4 months.

Ex-Vivo HSC Culture and Transplantation c-kit+ cells were isolated from adult mouse bone marrow and cultured in serumfree, cytokine-free defined medium for 7 days with (triangle) or without (circle) our formulation. After 7 days, the entire culture was transplanted to lethally irradiated mice (5/group) and survival was monitored over more than 16 weeks. All control animals (cultured without additives or no transplant) died within 17 days. Mice receiving bone marrow cells cultured in cytokine-free, serum-free medium with additives survived over 16 weeks. The experiment has been repeated 3 times. Erythrocytic, myelocytic, lymphocytic, and megakaryocytic lineages were present in peripheral blood and bone marrow after 4 months. These experiments demonstrated multilineage reconstitution, and further demonstrated that transplanted cells support long-term repopulation by transplanting to a secondary recipient. The results of these experiments are depicted in FIG. 13.

Example 10

Ex Vivo Culture of HSCs from Human Umbilical Cord Blood

Figure 14:
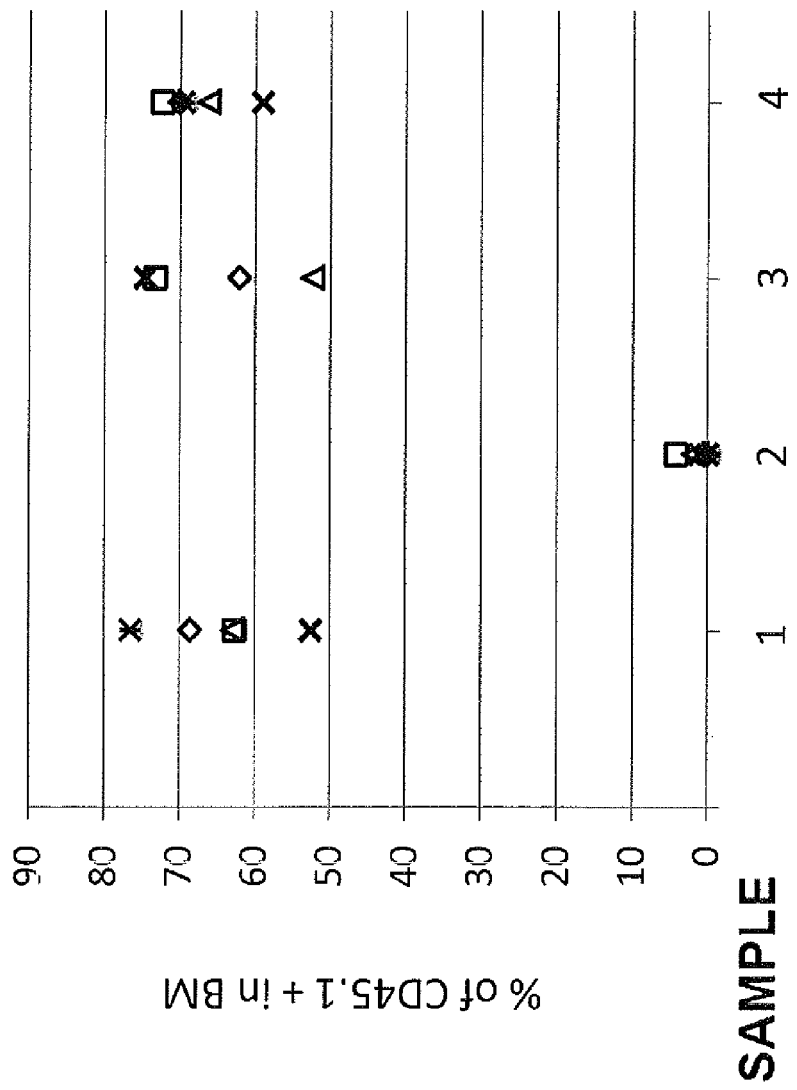
FIG. 14 demonstrates ex vivo culturing of HSCs from human umbilical cord blood. CD34+ cells from human UCB were isolated and either transplanted immediately to NSG mice (sample 1) or cultured in the cytokine-free, serum-free medium alone (sample 2), supplemented with our non-protein additives (sample 3), or with conventional cytokine cocktail (sample 4, includes IL3, SCF, FL, and Tpo) for either 4 days (shown) or 7 days (not shown). CD34+ cells increased 2-3 fold after one week when cultured with additives compared to no additives. Samples 2-4 were transplanted to NSG mice. Mice were bled monthly for flow cytometric analysis of human/mouse chimerism in peripheral blood (not shown) and were sacrificed at 4 months for flow cytometric analysis of human/mouse chimerism in bone marrow. The percent of human CD45.1 over total mononuclear cells in the bone marrow effluent is shown for each group. There were 5 mice per group and the experiment has been repeated with similar results 3 times. Secondary transplantation showed that human cells in group 3, but none of the other groups, sustained long-term repopulating activity for myelocytic, erythrocytic, and lymphocytic lineages.

CD34+ cells isolated from human umbilical cord blood have been cultured for either 4 or 7 days in ex vivo-15 medium supplemented with GSK-3 inhibitor and rapamycin, and then transplanted to non-lethally irradiated NODSCID/NSG (immunocompromised) mice and evaluated human/mouse chimerism. As depicted in FIG. 14, CD34+ cells cultured without cytokines but with GSK-3 inhibitor+mTOR inhibitor were as effective in repopulating NSG mice as cells not cultured or cells cultured with cytokines. Furthermore, the cells cultured in GSK-3 inhibitor+rapamycin supported long-term repopulating activity in secondary transplantation, whereas the cytokine treated cells did not support secondary transplants.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method for the maintenance and expansion of a hematopoietic stem cell (HSC), the method comprising culturing said HSC in a medium comprising at least one glycogen synthase kinase-3 (GSK-3) inhibitor and at least one mammalian target of rapamycin (mTOR) inhibitor, wherein the multipotentiality of the HSC is retained during the culturing.

2. The method of claim 1, wherein the HSC is derived from a mammal.

3. The method of claim 1, wherein the mammal is a human.

4. The method of claim 1, wherein exogenous genetic material has been introduced into the HSC.

5. The method of claim 1, wherein the medium further comprises at least one cytokine.

6. The method of claim 1, wherein the medium further comprises a promotion factor.

7. The method of claim 1, wherein the GSK-3 inhibitor is lithium, or a salt thereof.

8. The method of claim 1, wherein the mTOR inhibitor is rapamycin.

9. The method of claim 1, wherein the culturing is ex vivo.

* * * * *